US012779066B2

(12) United States Patent
Kim et al.

(10) Patent No.: US 12,779,066 B2
(45) Date of Patent: Nov. 3, 2026

(54) STERILIZATION DEVICE THAT IS HARMLESS TO HUMAN BODY

(71) Applicant: NANO CMS CO., LTD., Chungcheongnam-do (KR)

(72) Inventors: Shi Surk Kim, Chungcheongnam-do (KR); Seong Uk Lee, Chungcheongnam-do (KR); Sung Jin Park, Champaign, IL (US)

(73) Assignee: NANO CMS CO., LTD. (KR)

( * ) Notice: Subject to any disclaimer, the term of this patent is extended or adjusted under 35 U.S.C. 154(b) by 420 days.

(21) Appl. No.: 18/286,021

(22) PCT Filed: Feb. 18, 2022

(86) PCT No.: PCT/KR2022/002400

§ 371 (c)(1),
(2) Date: Oct. 6, 2023

(87) PCT Pub. No.: WO2022/177337

PCT Pub. Date: Aug. 25, 2022

(65) Prior Publication Data

US 2024/0181098 A1 Jun. 6, 2024

(30) Foreign Application Priority Data

Feb. 19, 2021 (KR) ........................ 10-2021-0022275
Aug. 10, 2021 (KR) ........................ 10-2021-0105703
Feb. 17, 2022 (KR) ........................ 10-2022-0020788

(51) Int. Cl.
*A61L 2/10* (2026.01)
*A61L 2/24* (2006.01)
*A61L 103/05* (2026.01)

(52) U.S. Cl.
CPC *A61L 2/10* (2013.01); *A61L 2/24* (2013.01); *A61L 2103/05* (2026.01); *A61L 2202/11* (2013.01); *A61L 2202/14* (2013.01)

(58) Field of Classification Search
CPC ........................................................ A61L 2/10
See application file for complete search history.

(56) References Cited

U.S. PATENT DOCUMENTS 11,020,498 B2 6/2021 Rosen et al.
11,135,324 B2 10/2021 Rosen et al.
(Continued)

FOREIGN PATENT DOCUMENTS

JP 2014508819 4/2014
JP 2021010403 2/2021
(Continued)

OTHER PUBLICATIONS

Buonanno, Manuela, et al., "Germicidal Efficacy and Mammalian Skin Safety of 222-nm UV Light," Radiation Research, vol. 187, pp. 493-501 (2017) 2017.
(Continued)

*Primary Examiner* — Kevin Joyner

(57) ABSTRACT

A sterilization device has an ultraviolet light unit including an ultraviolet light source and a filter for filtering wavelengths of 230 to 270 nm, emitted from the ultraviolet light source; a lighting unit including an LED light source; and a control unit which controls on and off of the ultraviolet light unit and the lighting unit and supplies power, wherein the filter includes a nanophosphor which is 3 nm or less and converts the light having a wavelength of 230 to 270 nm into light of another wavelength.

9 Claims, 22 Drawing Sheets

(56) References Cited

U.S. PATENT DOCUMENTS

| | | | | |
|---|---|---|---|---|
| 2013/0289132 | A1 | 10/2013 | Greuel et al. | |
| 2016/0121007 | A1* | 5/2016 | Dayton | A61L 2/10 250/492.1 |
| 2019/0255201 | A1 | 8/2019 | Rosen et al. | |
| 2020/0215210 | A1 | 7/2020 | Rosen et al. | |
| 2020/0215214 | A1 | 7/2020 | Rosen et al. | |
| 2020/0230271 | A1* | 7/2020 | Choi | F21V 33/0012 |
| 2021/0283282 | A1 | 9/2021 | Rosen et al. | |
| 2021/0318168 | A1* | 10/2021 | Ramer | G01J 1/38 |
| 2022/0062463 | A1* | 3/2022 | Ramer | H05B 47/16 |

FOREIGN PATENT DOCUMENTS

| | | |
|---|---|---|
| KR | 20030063073 | 7/2003 |
| KR | 101607277 | 3/2016 |
| KR | 20160109172 | 9/2016 |
| KR | 20190015963 | 2/2019 |
| KR | 102093720 | 5/2020 |
| KR | 20200123453 | 10/2020 |
| KR | 102260627 | 6/2021 |

OTHER PUBLICATIONS

Abstract of JP 2014-508819 2023.
Abstract of JP 2021-010403 2023.
Abstract of KR 10-2093720 2023.
Abstract of KR 10-2260627 2023.
Abstract of KR 2003-0063073 2023.
Abstract of KR 2016-0109172 2023.
Abstract of KR 2019-0015963 2023.
Abstract of KR 2020-0123453 2023.
OA against KR 2021-0105703 (Oct. 19, 2021) 2021.
OA Against KR 2022-0020788 (Jul. 13, 2022) 2022 .
Qui, Baotian, et al., "Synthesis and enhanced luminescent properties of SiO2@LaPO4:Ce3+/Tb3+ microspheres," Optical Materials Express, vol. 8, No. 1, pp. 59-65, Jan. 2018. 2018.
PCTISA210 issued for PCT/KR2022/002400 (Jun. 10, 2022) 2022.
PCTISA237 issued for PCT/KR2022/002400 (Jun. 10, 2022).
PCT ISA220 issued for PCT/KR2022/002400 (Jun. 10, 2022).

* cited by examiner

| Particle size (nm) | Absorption intensity | Emission intensity | Wavelength transmittance at 220 nm (%) |
|---|---|---|---|
| 3 nm or less | 36,000 | 38,006 | 69.73 |
| 60 nm | 21,424 | 21,905 | 26.73 |
| 200 nm or more | 10,094 | 9,406 | 5.73 |

STERILIZATION DEVICE THAT IS HARMLESS TO HUMAN BODY

PRIORITY

This application is a National Stage filing under 35 U.S.C. § 371 of, and claims priority via, International Application No. PCT/KR2022/002400, filed Feb. 18, 2022; pursuant to 35 U.S.C. § 119, this application also claims the benefit of earlier filing date and right of priority to Korean Patent Application Number 10-2021-0022275, filed on Feb. 19, 2021; and pursuant to 35 U.S.C. § 119, this application also claims the benefit of earlier filing date and right of priority to Korean Patent Application Number 10-2021-0105703, filed on Aug. 10, 2021, this application also claims the benefit of earlier filing date and right of priority to Korean Patent Application Number 10-2022-0020788, filed on Feb. 17, 2022. The entire content of PCT/KR2022/002400 is hereby incorporated by reference. The entire content of Korean Patent Application Number 10-2021-0022275, Korean Patent Application Number 10-2021-0105703, and Korean Patent Application Number 10-2022-0020788 are hereby incorporated by reference.

BACKGROUND

A technique of sterilizing by irradiating ultraviolet rays is known. For example, it is known that DNA exhibits the highest absorption characteristics around the wavelength of 260 nm. A low-pressure mercury lamp exhibits a high emission spectrum around the wavelength of 254 nm. For this reason, a technique of sterilizing using a mercury lamp is widely used. However, it is known that when the human body is irradiated with ultraviolet rays of such a wavelength range, there is a risk of affecting the human body.

The skin is divided into three parts an epidermis, a dermis, and a subcutaneous tissue of the deep part in order from the part closer to the surface, and the epidermis is divided into four layers: a stratum corneum, a granular layer, a spinous layer, and a basal layer, in order from the part further closer to the surface. When ultraviolet rays having a wavelength of 254 nm are irradiated to the human body, they penetrate the stratum corneum to reach the granular layer, the spinous layer, and in some cases the basal layer, and are absorbed by the DNA of cells present in these layers. As a result, there is a problem of causing skin cancer.

A technical subject to be solved by the present invention is to provide a sterilization device and a sterilization lamp that are harmless to the human body.

In order to solve the above technical problem, a sterilization lamp according to an embodiment of the present invention comprises: an ultraviolet light unit including an ultraviolet light source and a filter for filtering wavelengths of 230 to 270 nm being emitted from the ultraviolet light source; a lighting unit including an LED light source; and a control unit which controls on and off of the ultraviolet light unit and the lighting unit and supplies power, wherein the filter includes a nanophosphor which is 3 nm or less and converts the light having a wavelength of 230 to 270 nm into a light of another wavelength.

In addition, the nanophosphor may include $LaPO_4:Ce^{3+}\cdot Tb^{3+}$.

In addition, the control unit controls the ultraviolet light unit to operate for a first time period, wherein in the middle of the operation during the first time, the control unit may control the ultraviolet light to include one or more rest periods in which the ultraviolet light unit is turned off for a second time period.

In addition, the control unit may turn off the ultraviolet light unit and display replacement information for the ultraviolet light unit when the cumulative operating time of the ultraviolet light unit is greater than or equal to a threshold value.

In addition, a display unit for displaying operation information of the ultraviolet light unit is included, wherein it is displayed in a first color when the ultraviolet light unit is operating, wherein a second color is displayed when the accumulated operating time of the ultraviolet light unit is greater than or equal to a threshold value, and wherein the second color may flicker when the ultraviolet light unit is not operating normally.

In addition, it includes: a switching element for turning on and off the ultraviolet light unit; and a temperature sensor for measuring a temperature inside the switching element, a substrate on which the switching element or a sterilization lamp is mounted, wherein the control unit may turn off ultraviolet light unit when the temperature measured by the temperature sensor is greater than or equal to a threshold value.

In addition, a motion detection sensor for detecting motion in a predetermined region is included, and the control unit may turn on the ultraviolet light unit according to the motion detection of the motion detection sensor.

In addition, a housing in which the ultraviolet light unit, lighting unit, and control unit are disposed therein is included, wherein the housing includes a cover glass located at an upper portion of the housing and being formed with an ultraviolet light unit accommodating unit for accommodating the ultraviolet light unit at the center thereof, and wherein the ultraviolet light unit accommodating unit may include a coupling unit to which the ultraviolet light unit is detachably attachable.

The LED light source may be disposed at a lower portion of a circumferential region of the ultraviolet light unit accommodating unit of the cover glass.

In order to solve the above technical subject, a sterilization device according to an embodiment of the present invention comprises: a planar lamp in which at least one or more light sources emitting ultraviolet rays are disposed at an inner region; a filter being coated or laminated on a light-exiting surface of the lamp to filter light having a wavelengths of 230 to 270 nm; and a power supply unit supplying power to the lamp, wherein the filter includes a nanophosphor having a size of 3 nm or less to convert light having a wavelengths of 230 nm to 270 nm into a light having a different wavelength.

In addition, the nanophosphor may include $LaPO_4:Ce^{3+}\cdot Tb^{3+}$.

In addition, the power supply unit may include a front electrode layer and a rear electrode layer respectively bonded to upper and lower portions of the lamp to supply power to the lamp, wherein the front electrode layer may have a hole through which the light of the lamp passes.

In addition, the nanophosphor can convert a light having wavelengths of 230 to 270 nm into a light having a wavelength of 550 nm.

In addition, the filter may include a filter that blocks light having wavelengths of 230 to 270 nm by deposition.

In addition, the filter may include a filter that blocks light having wavelengths of 230 to 270 nm by deposition of Sn and Al.

In addition, at least one or more of the light sources emitting ultraviolet light may be a 222 nm KrCl excimer light source.

In addition, conductive lines are formed at an edge region of the lamp, and the front electrode layer and the rear electrode layer may be in contact with the conductive lines to supply power.

In addition, it further include: an inclination sensor for measuring the inclination of the lamp; and a housing having a handle portion that can be gripped by a user, wherein the supply of power to the lamp may be cut off when an inclination being measured by the inclination sensor exceeds 75 degrees.

In addition, it further includes a counter for counting time from the time when a power is applied to the lamp, and if the time of the counter is greater than or equal to a threshold value, the supply of power to the lamp can be cut off.

According to embodiments of the present invention, it is possible to provide a sterilization device and a sterilization lamp that are harmless to the human body while killing viruses and bacteria.

DETAILED DESCRIPTION OF THE DRAWINGS

Hereinafter, preferred embodiments of the present invention will be described in detail with reference to the accompanying drawings.

However, the technical idea of the present invention is not limited to some embodiments to be described, but may be implemented in various forms, and inside the scope of the technical idea of the present invention, one or more of the constituent elements may be selectively combined or substituted between embodiments.

In addition, the terms (including technical and scientific terms) used in the embodiments of the present invention, unless explicitly defined and described, can be interpreted as a meaning that can be generally understood by a person skilled in the art, and commonly used terms such as terms defined in the dictionary may be interpreted in consideration of the meaning of the context of the related technology.

In addition, terms used in the present specification are for describing embodiments and are not intended to limit the present invention.

In the present specification, the singular form may include the plural form unless specifically stated in the phrase, and when described as "at least one (or more than one) of A and B and C", it may include one or more of all combinations that can be combined with A, B, and C.

In addition, in describing the components of the embodiment of the present invention, terms such as first, second, A, B, (a), and (b) may be used. These terms are merely intended to distinguish the components from other components, and the terms do not limit the nature, order or sequence of the components.

And, when a component is described as being 'connected', 'coupled' or 'interconnected' to another component, the component is not only directly connected, coupled or interconnected to the other component, but may also include cases of being 'connected', 'coupled', or 'interconnected' due that another component between that other components.

In addition, when described as being formed or arranged in "on (above)" or "below (under)" of each component, "on (above)" or "below (under)" means that it includes not only the case where the two components are directly in contact with, but also the case where one or more other components are formed or arranged between the two components. In addition, when expressed as "on (above)" or "below (under)", the meaning of not only an upward direction but also a downward direction based on one component may be included.

Figure 1:
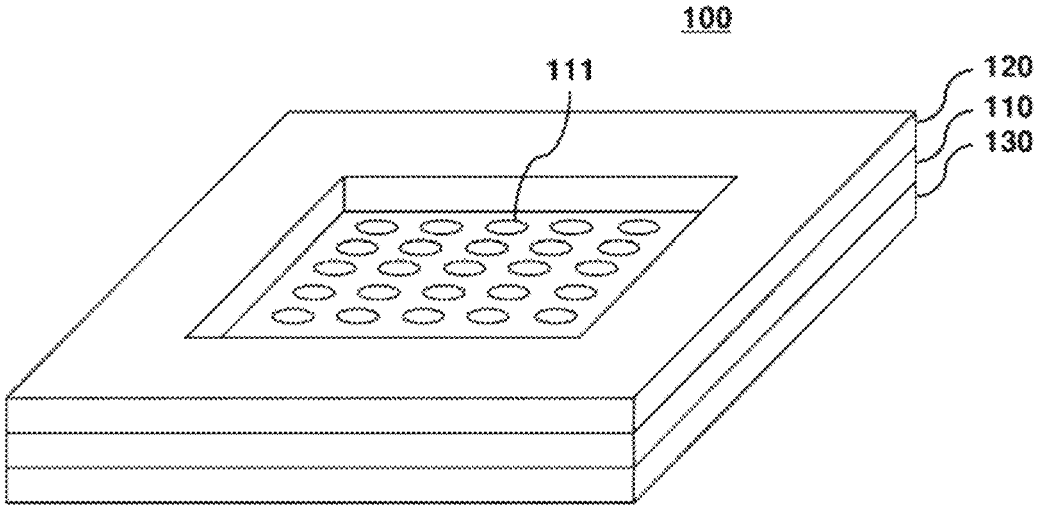
FIG. 1 illustrates a sterilization device according to an embodiment of the present invention.
Figure 2:
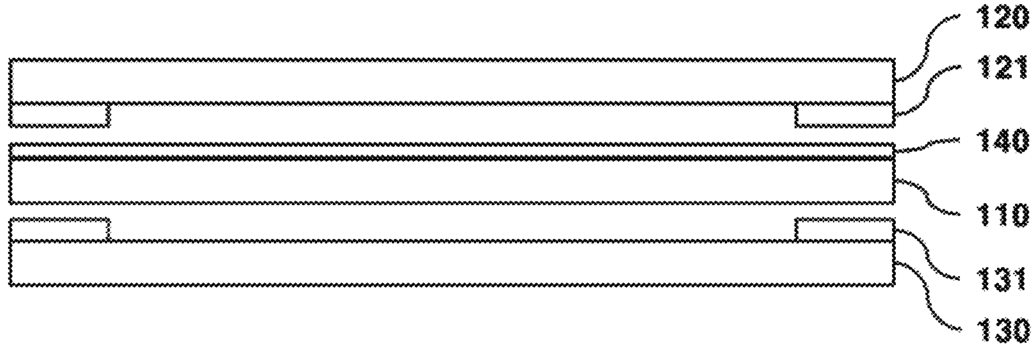
FIGS. 2 to 16 are views for explaining a sterilization device according to an embodiment of the present invention.

FIG. 1 is a perspective view of a sterilization device according to an embodiment of the present invention, and FIG. 2 is a side view of a sterilization device according to an embodiment of the present invention.

The sterilization device 100 according to an embodiment of the present invention comprises a lamp 110 and a filter 140, and may further include a front electrode layer 120, a rear electrode layer 130, a power cutoff unit (not shown) or an inclination sensor (not shown) and the like.

The lamp 110 includes at least one or more of a light source 111 emitting ultraviolet rays, and the light source 111 is disposed at an inner region. Sterilization or pasteurization is performed using emitted ultraviolet rays. The lamp 110 is formed in a flat shape and emits surface light. A uniform sterilization area can be realized through surface light emission. The shape of the lamp may be a rectangle or a circle, and may be formed in various shapes such as a square column or a cylinder.

In order to kill viruses, bacteria, and the like, a lamp 110 emitting ultraviolet rays is formed. Here, the lamp 110 may emit ultraviolet rays having wavelengths of 200 to 230 nm. The lamp 110 may be an excimer lamp (microplasma lamp) using KrCl as a light emitting gas. In addition, the lamp may be a variety of lamps emitting ultraviolet rays.

Halogen gas (fluorine, chlorine, etc.) and dilute gas (krypton, xenon, etc.) are combined by high voltage discharge and the like to create excimer molecules. When excimer molecules decay, they emit ultraviolet light, which is used as an excimer laser. An excimer lamp uses a technology in which a high-voltage electric field is formed in a quartz tube filled with a combination of inert gas and halogen gas to induce molecular dissociation of the internal gas, and emits a single wavelength in the UV-C region enabling irradiation treatment with a desired wavelength depending on the gas composition. In addition, it has a light intensity corresponding to the existing UV-C low-pressure lamp, so it is easy to apply to the actual food sterilization process, so attention is focused as a next-generation mercury-free UV-C light source. Among various wavelengths, the 222 nm wavelength light of KrCl gas shows high sterilization efficiency. Light having a wavelength of 222 nm has a sterilizing effect that removes viruses, bacteria, and spores. The KrCl excimer light source emits ultraviolet light having a peak at a wavelength of 222 nm. At this time, not only light with wavelengths around the 222 nm wavelength, but also light with wavelengths above 230 nm are emitted.

A light having wavelengths of 230 to 270 nm is toxic and, when irradiated to the human body, has a harmful effect on the human body, such as causing skin cancer. The skin is divided into three parts an epidermis, a dermis, and a subcutaneous tissue of the deep part in order from the part closer to the surface, and the epidermis is divided into four layers a stratum corneum, a granular layer, a spinous layer, and a basal layer, in order from the part further closer to the surface. A light having a wavelength of 222 nm does not penetrate the stratum corneum even when irradiated to the human body, but a light having a wavelength of 230 nm or more, for example, 254 nm, penetrates the stratum corneum, reaching the granular layer or the stratum corneum, and in some cases the basal layer, and is absorbed into the DNA of cells present in these layers, which can cause skin cancer and the like. When a light having wavelengths of 230 to 270 nm is irradiated to an eye, keratitis or the like may occur. Therefore, a small amount of a light having wavelengths of 230 to 270 nm being emitted from the KrCl excimer lamp should be removed.

Figure 3:
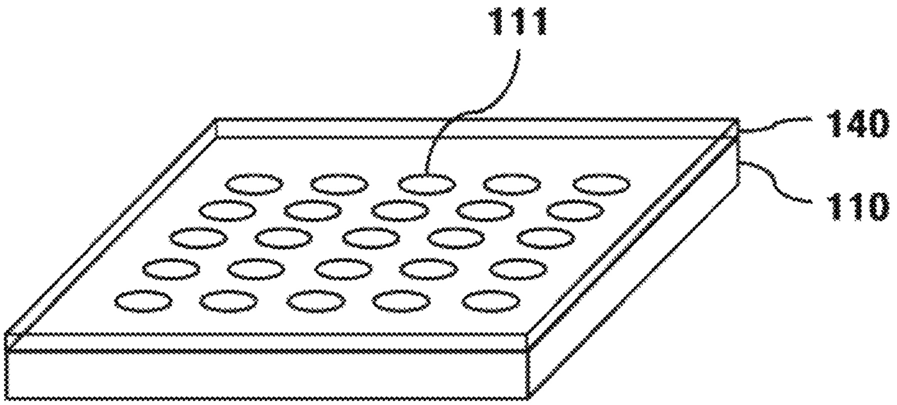

The filter 140 is coated or laminated on the light-exiting surface of the lamp 110 to filter wavelengths of 230 to 270 nm. The wavelengths of 230 to 270 nm can be filtered. The filter 140 is formed on the surface of the lamp 110 to filter wavelengths of 230 to 270 nm being emitted from the lamp 110 to prevent light having a wavelength harmful to the human body from being emitted to the outside. As shown in FIG. 3, the filter 140 may be stacked in a planar shape on the light-exiting surface of the lamp 110, and is transparent or translucent so that a light having wavelengths of 200 to 230 nm is transmitted. As such, sterilization is possible using a light having wavelengths of 200 to 230 nm transmitted through the filter 140. In particular, it is possible to sterilize by removing viruses, bacteria, spores, and the like using a light having a wavelength of 222 nm.

Figure 4:
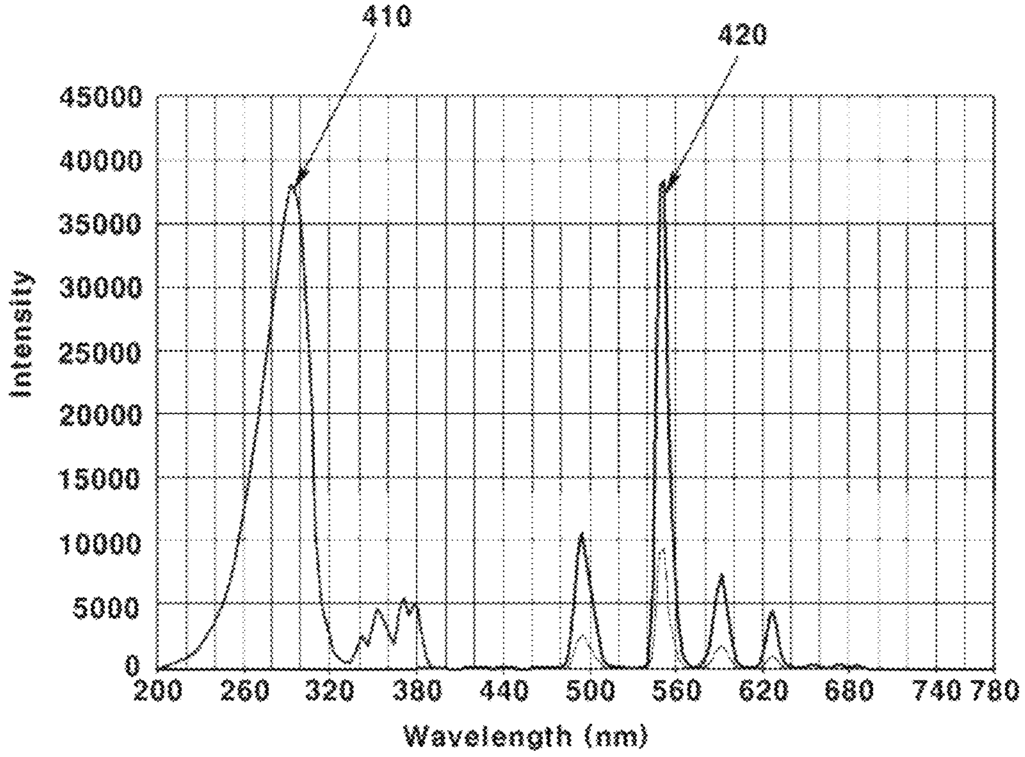

The filter 140 may convert or absorb a light having wavelengths of 230 to 270 nm into a light having a different wavelength in order to prevent light having wavelengths of 230 to 270 nm from being emitted through the filter 140. Or, it can be reflected. The filter 140 may include a nanophosphor that converts light having wavelengths of 230 to 270 nm into a light having a different wavelength. Here, the nanophosphor may convert a light having wavelengths of 230 to 270 nm into a light having a wavelength of 550 nm. As shown in FIG. 4, the nanophosphor included in the filter 140 may be a nano-fluorescent material that converts wavelengths (410) of 230 to 270 nm into a wavelength (420) of 550 nm. The nanophosphor may include $LaPO_4:Ce^{3+}\cdot Tb^{3+}$. Here, $LaPO_4:Ce^{3+}\cdot Tb^{3+}$ is the chemical structure of nanophosphor, and $LaPO_4:Ce^{3+}\cdot Tb^{3+}$ has a characteristic of absorbing a light having wavelengths of 230 to 270 nm and emitting a light having a wavelength of 550 nm. That is, it converts a light having wavelengths of 230 to 270 nm, which is toxic, into a light having a wavelength of 550 nm, which is harmless.

The nanophosphor may be formed into particles of a predetermined size, and may be mixed with a polymer material such as urethane, resin, or resin to form a filter 140. The nanophosphor may be formed with particle sizes of 0.1 to 5 nm or less, and may be formed with a particle size of 3 nm or less. Or, the nanophosphor may be stacked on an upper portion or a lower portion of a polymer layer containing a polymer material. At this time, it may be formed to have a thickness of 0.1 to 20 nm, and may be formed in a planar shape by a stacking method such as coating. It is natural that nanophosphor particles can be formed in various sizes, ratios, or thicknesses that convert a light having wavelengths of 230 to 270 nm into a light having other wavelengths.

The filter 140 may include a thin film coating that blocks a predetermined range of light. In addition to or together with the method of converting the wavelength of a light using nanophosphor, it is possible to block light of a specific wavelength. Here, the thin film coating may be a thin film containing aluminum (Al) and tin (Sn) that blocks the light having wavelengths of 230 to 270 nm. At this time, the thin film coating can be formed by mixing aluminum and tin to form a thin film, or formed of an aluminum thin film layer and a tin thin film layer. When aluminum and tin are mixed, the proportion of tin may be 0.01 to 40% or 0.01 to 20%. The remaining proportion may be aluminum or may further include other additives and the like. When formed of an aluminum thin film layer and a tin thin film layer, each thin film layer may be formed in a planar shape, and a tin thin film layer may be formed at an upper portion of the aluminum thin film layer or an aluminum thin film layer may be formed at an upper portion of the tin thin film layer. Or, one or more tin thin film layers and one or more aluminum thin film layers may be sequentially formed. The thickness of the thin film layer of tin may be 0.1 to 30 Å (angstroms) or 0.0001 to 20 Å. The aluminum thin film layer may have a thickness of 0.1 to 30 Å or more. Here, it is natural that the mixing ratio of aluminum and tin forming the thin film coating or the thickness of the aluminum thin film layer and the tin thin film layer may be variously formed to a mixing ratio or thickness that blocks lights having wavelengths of 230 to 270 nm.

A filter 140 may be formed as a thin film coating at an upper portion of the polymer material layer containing the nanophosphor particles. By using nanophosphor and thin film coating, a light having wavelengths of 230 to 270 nm, which is toxic, is converted, and may block a light having wavelengths of 230 to 270 nm. By converting a light having wavelengths of 230 to 270 nm, which is toxic, into a light having a different wavelength using nanophosphor, and at the same time, by blocking lights having wavelengths of 230 to 270 nm using a thin film coating, the lights having toxic wavelengths affecting the human body can be safely blocked in two ways.

FIGS. 5 to 8 are diagrams showing experimental results of a sterilization device to which a filter is applied.

Figure 5:
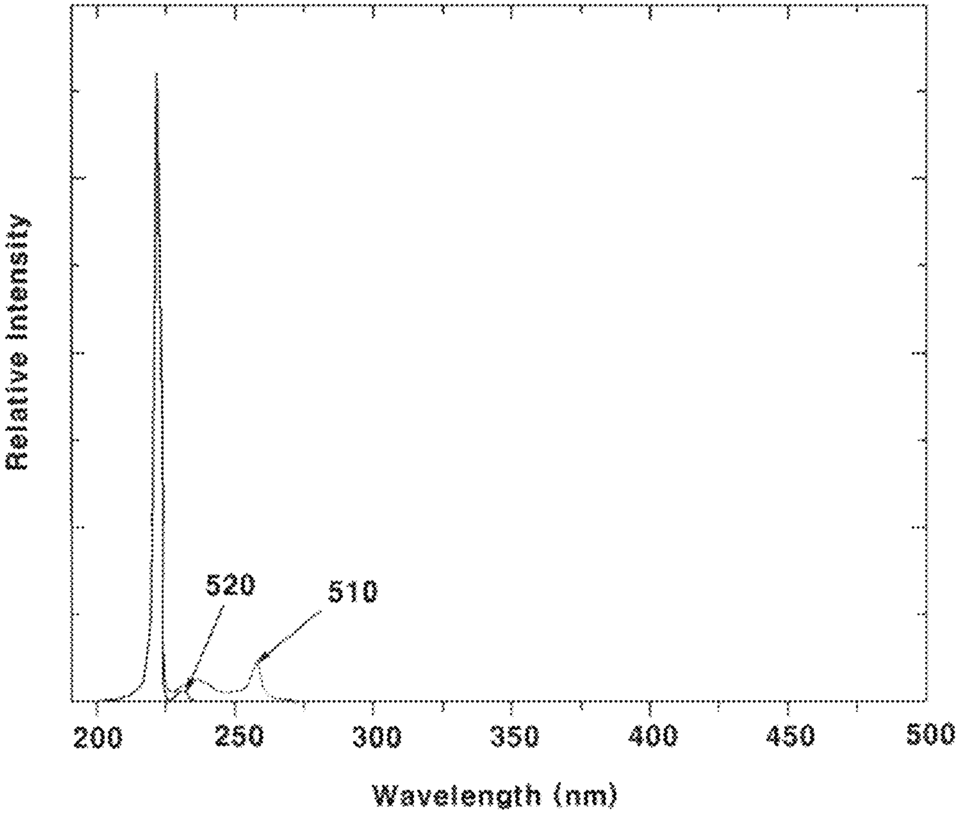

FIG. 5 is a comparison of a wavelength of a lamp without a filter 140 and a wavelength thereof with a filter 140 being applied thereto, and when the filter is not applied (510), lights having wavelengths of 230 to 270 nm, which is toxic, is emitted. The amount of lights having wavelengths of 230 to 270 nm is small compared to total light, but may have a significant adverse effect on the human body. On the other hand, when a filter is applied (520), it can be confirmed that toxic light having wavelengths of 230 to 270 nm are blocked or reduced to an extent harmless to the human body.

Figure 6:
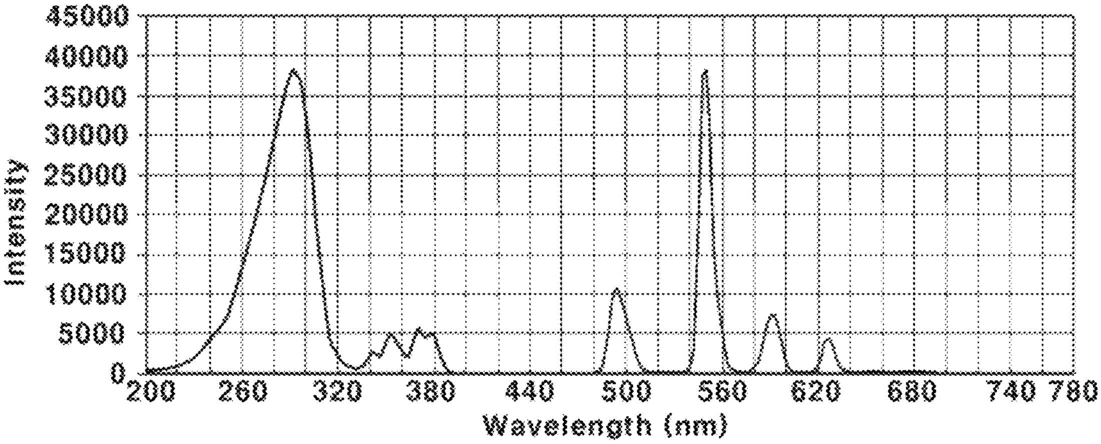
Figure 7:
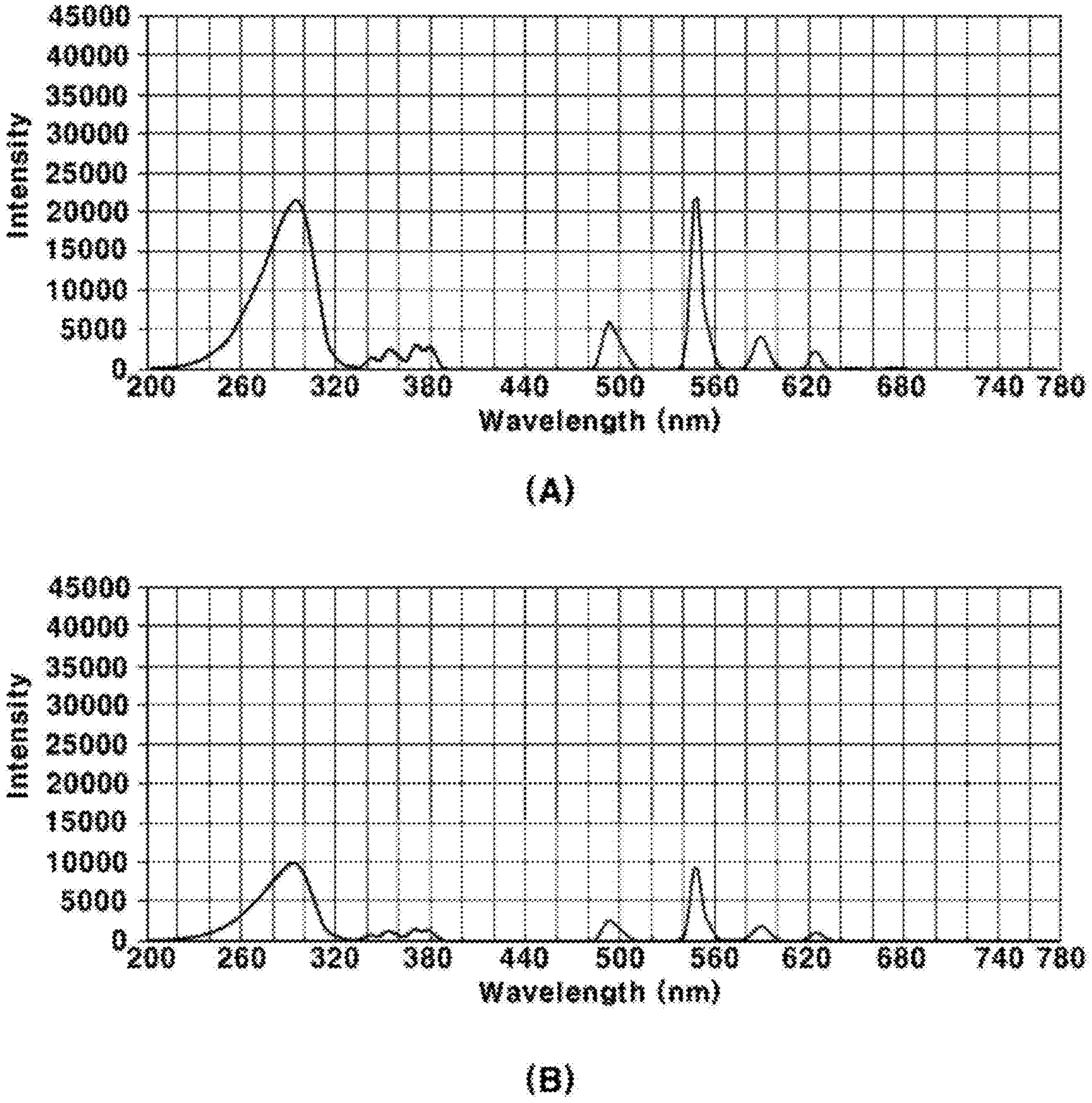

FIG. 6 is a graph of photo luminescence measurement values when a filter containing nanophosphor ($LaPO_4:Ce^{3+}\cdot Tb^{3+}$) having a particle size of 3 nm or less is applied, and FIG. 7(A) is a graph of photo luminescence measurement values when a filter containing nanophosphor having a particle size of 60 nm is applied. Here, the particle size 60 nm is the average particle size of nanophosphor, and it is a graph of the photo luminescence measurement values when having particle sizes of 10 to 110 nm. FIG. 7(B) is a graph of photo luminescence measurement values when a filter containing nanophosphor having a particle size of 200 nm or more is applied.

Figure 8:
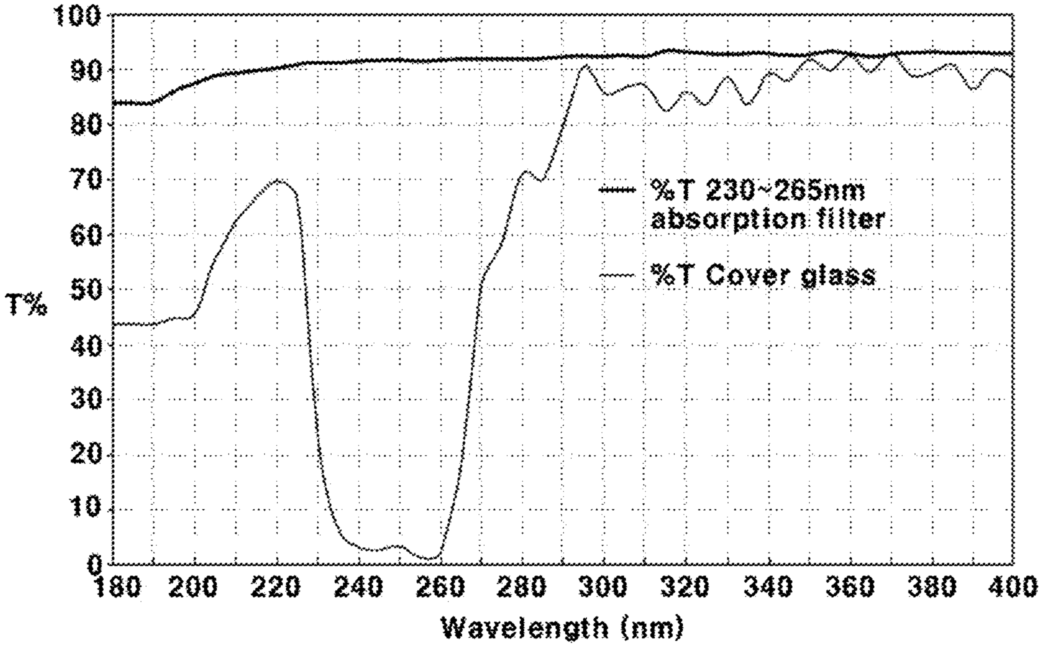
Figure 9:
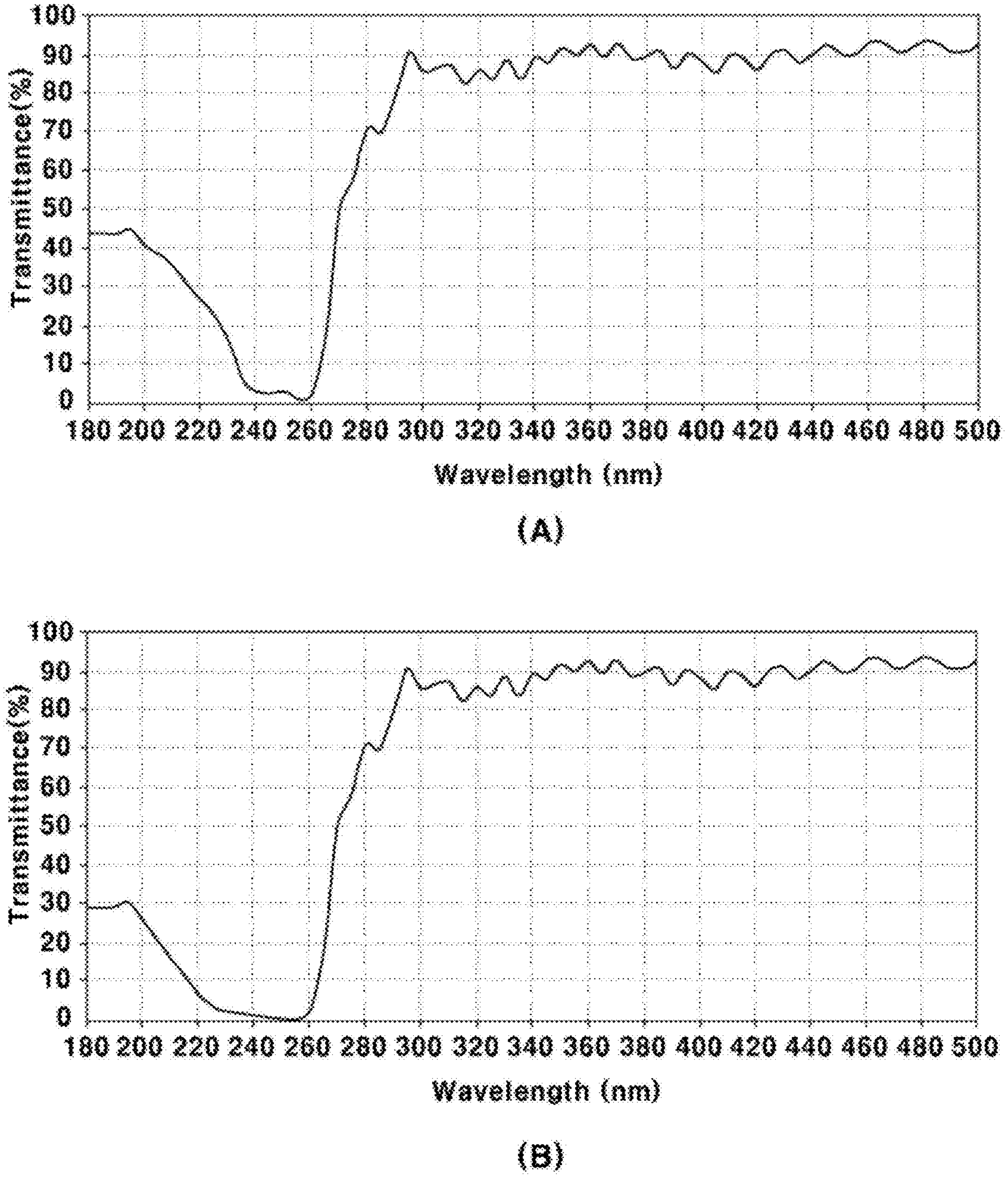
Figures 10, 11:
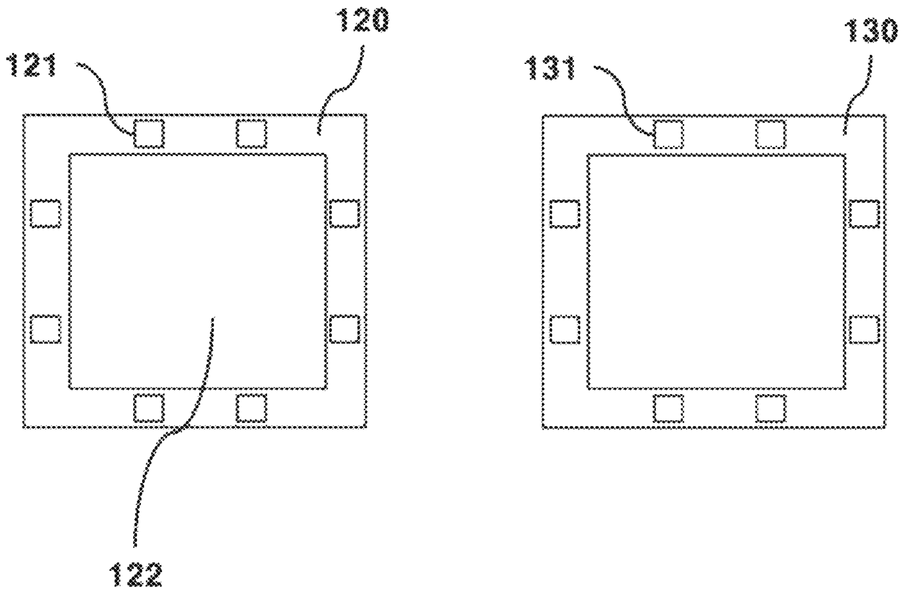

FIG. 8 is a graph of Band Pass % T when a filter containing nanophosphor ($LaPO_4:Ce^{3+}\cdot Tb^{3+}$) having a particle size of 3 nm or less is applied compared to the case where only glass is applied; FIG. 9(A) is a graph of Band Pass % T when a filter containing nanophosphor having a particle size of 60 nm is applied; and FIG. 9(B) is a graph of band pass % T when a filter containing nanophosphor having a particle size of 200 nm or more is applied. FIG. 10 is the results of absorption intensity, emission intensity, and transmittance at a wavelength of 222 nm for each particle size of each case.

It can be seen that all three cases filter wavelengths of 230 to 270 nm, but the luminous intensity and the degree of transmission at the 222 nm wavelength, which is the wavelength for sterilization, are different. Below 3 nm, the emission intensity is 38,006, transmittance at 222 nm is 69.73%, but above 60 nm, emission intensity is 21,905, transmittance at 222 nm is 26.73%, and above 200 nm, emission intensity is 9,406, transmittance at 222 nm is 5.73%, and as the light of 200 nm to 230 nm in the far ultraviolet region does not pass through, the sterilization function is lowered and the function of the micro plasma lamp at 222 nm is lost. For sterilization, wavelength transmittance at 222 nm must be 60% or more to be sterilized, so nanophosphor ($LaPO_4:Ce^{3+}\cdot Tb^{3+}$) with a particle size of 3 nm or less must be included to be used as a sterilization device. In particular, when applying to the human body, when irradiating for more than a critical time, for example, 8 hours or more, health problems may occur, so that wavelength transmittance at 222 nm is important so that sterilization can be achieved only by irradiation within the critical time. In the case of using nanophosphor ($LaPO_4:Ce^{3+}\cdot Tb^{3+}$) with a particle size of 3 nm or less, 60% or more of wavelength transmittance at 222 nm appears, and sterilization is possible while maintaining safety to the human body. The lamp 110 may include a light source emitting ultraviolet light as well as a light source emitting light of a different wavelength. By including a light source that emits not only ultraviolet rays for sterilization but also other wavelengths of light for lighting and the like, both sterilization and illumination functions can be performed. At this time, a light source emitting visible light or infrared light may be included, and a light source such as LED may be included. A light source emitting ultraviolet rays for sterilization and a light source emitting light for lighting may be formed by dividing regions. A light source emitting ultraviolet rays may be disposed inside, and a light source emitting light for illumination may be disposed externally or vice versa. Or, a plurality of light sources may be disposed next to each other in between without dividing regions, or may be disposed in various shapes.

The front electrode layer 120 is bonded to an upper portion of the lamp 110 and the rear electrode layer 130 is bonded to a lower portion of the lamp 110 to supply power to the lamp. The front electrode layer 120 is formed at an upper portion of the lamp 110 in a direction in which light is emitted from the lamp 110 and is bonded to the lamp 110. At this time, as shown in FIG. 11, the electrode 121 is formed on a surface being bonded to the lamp 110, and can be bonded to the lamp 110 through the electrode 121. The front electrode layer 120 has a hole 122 through which light from the lamp 110 passes so as not to interfere with irradiation of light being emitted from the lamp 110.

The rear electrode layer 130 is formed at a lower portion of the lamp 110 in a direction opposite to the direction in which light is emitted from the lamp 110 and is bonded to the lamp 110. At this time, the electrode 131 is formed on a surface to be bonded to the lamp 110, and it can be bonded to the lamp 110 through the electrode 131. A hole may also be formed in the rear electrode layer 130 to correspond to the front electrode layer 120.

The front electrode layer 120 and the rear electrode layer may be formed of a PCB board, and a connector to which power is supplied from the outside may be formed. By supplying power being inputted through the connector to the lamp 110 through the electrodes 121 and 131, light for sterilization can be emitted to the outside.

When bonding the front electrode layer 120 and the rear electrode layer 130 to the lamp, when using an electrode being printed with a gold having a thickness of several micrometers, the electrodes may be formed by using a clamp because the welding method using gold or nano-metal is not easy, however, productivity may decrease. In order to increase productivity and stability of quality, an electrode may be formed using a gasket, which is a halogen-free material having excellent heat resistance, electrical conductivity, compression resilience, and solder wettability. Through this, it is possible to increase productivity and stability of quality.

A light source may be formed inside the lamp 110, and conductive lines may be formed at an edge region surrounding the light source. The light source may be formed in a circular or rectangular shape, and the conductive lines may also be formed in various shapes such as a circular or rectangular shape at an edge region. The conductive lines are conducting lines and may be formed by applying a metal or a conductive material. The electrode 121 of the front electrode layer 120 and the electrode 131 of the rear electrode layer 130 may be in contact with the conductive lines to supply power. The electrodes 121 of the front electrode layer 120 and the electrodes 131 of the rear electrode layer 130 may be formed at positions corresponding to the position of the conductive lines, as shown in FIG. 11, so as to be in contact with the conductive lines being formed at an edge region of the lamp.

One electrode of the electrode 121 of the front electrode layer 120 and the electrode 131 of the rear electrode layer 130 may be a (+) electrode and the other electrode may be a (−) electrode. Power can be supplied to the lamp 110 through conductive lines positioned between the (+) electrode and the (−) electrode by allowing a high-voltage current to flow through the (+) electrode and the (−) electrode.

Or, only one of the front electrode layer and the rear electrode layer may be formed to supply power to the lamp.

A sterilization device according to an embodiment of the present invention may be formed as a portable type. At this time, the portable sterilization device 200 according to an embodiment of the present invention may further include a housing 210 in which a handle unit 220 that can be gripped by a user is formed. The housing 210 may include one or more holes 211 in which an ultraviolet light source is formed and light is emitted therethrough.

Figure 12:
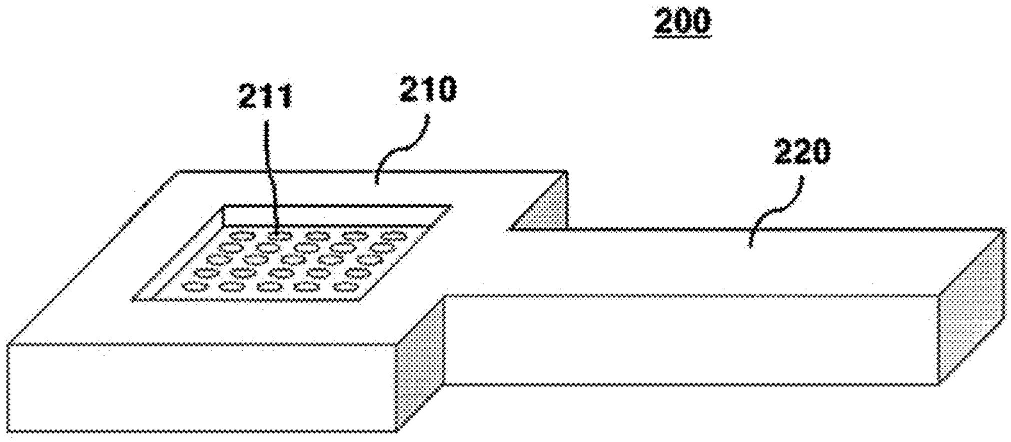

The housing may be formed in a variety of shapes such as lighting fixtures in addition to the shape shown in FIG. 12. It may be in the shape of a cylinder; a hook may be formed so that it can be installed on the ceiling; and a roller may be formed so that the position can be adjusted. In addition, an angle adjustment unit is formed to change the direction of light, and a height adjustment unit may be formed so that the height can be adjusted.

The portable sterilization device 200 can be freely irradiated with sterilizing light by being held by the user. When the sterilization device is located at an upper portion, such as a lamp, sterilization may be insufficient or not performed at a location where the path of light does not reach due to the straightness of ultraviolet rays. Sterilization can be efficiently performed by scanning a chair or a corner with the portable sterilization device 200 by forming the sterilization device as a portable type being formed with a handle unit.

At this time, although the filter 140 removes light of a wavelength harmful to the human body, it is preferable not to directly irradiate the human body for a long time. To this end, the front electrode layer 120 and the rear electrode layer 130 may cut off power supply to the lamp 110 when the inclination of the light-exiting surface to the ground exceeds 75 degrees. In order to prevent irradiation to a person, when the inclination exceeds 75 degrees or the light-exiting surface is directing upward, rather than directing downward, which is the ground direction, power supply is cut off to prevent light from being emitted, thereby increasing safety.

In order to check the degree of inclination, an inclination sensor for measuring the inclination of the lamp 110 and a power cut-off unit for cutting off the power supply to the lamp when the inclination measured by the inclination sensor exceeds 75 degrees may be further included. Here, the inclination sensor may be a gyro sensor or another sensor capable of measuring the degree of inclination. The power cut-off unit cuts off power supply to the lamp 110 when the inclination exceeds 75 degrees according to the sensing value of the inclination sensor. The power cut-off unit may be composed of a switch such as a relay. The switch may be an electrically operated electrical switch. Or, when the lamp 110 faces the ground, the electrode is connected to the conductive lines by gravity, and when the inclination of the lamp 110 exceeds 75 degrees, the downward force is reduced, so it can be a physical switch being formed with a spring that operates to separate the electrode from the conductive lines.

In addition, a counter for counting time from the time when power is applied to the conductive lines may be further included, and when the time of the counter is 10 seconds or more, power supply to the lamp may be cut off. Power is supplied to operate only for the time required for sterilization, and when a predetermined time elapses after the power is supplied, the supply of power to the lamp may be cut off. The power-off time may be set between 10 and 30 seconds.

A sterilization device according to an embodiment of the present invention is formed as a sterilization lamp and can be applied to various devices. A sterilization lamp according to an embodiment of the present invention includes an ultraviolet light source and a filter for filtering wavelengths of 230 to 270 nm being emitted from the ultraviolet light source. The filter may include a nanophosphor that converts light having wavelengths of 230 to 270 nm into a light having another wavelength, and the ultraviolet light source may be a 222 nm KrCl excimer lamp.

The sterilization lamp formed in this way can be applied to all means of transportation such as interior lights of automobiles. In the case of a vehicle, it can be installed on the ceiling, started before departure, sterilized for 10 to 20 seconds, and automatically flicker. In addition, it can be applied to a chair, a device that scans and sterilizes corners, a device for removing viruses in preparation for biological warfare portable by soldiers, a light fixture being installed inside a ship cabin, and a tank.

In addition, it can be applied to places where sterilization inside the operating room after surgery is required, such as hospitals. For example, when a covid-19 patient occurs in a nursing home (hospital) used by the elderly having reduced immune function, orthopedic surgery, traditional herbal medicine clinic, operating room in general hospital, emergency room, and the like, since it is difficult to treat the next emergency patient, first of all, it can be applied to the place where it is urgent to remove the risk factors of airborne infection. In addition, it can be installed in government offices, public health centers, temporary clinics, and the like, such as a ward office, a civil affairs office at a community center, and it can be installed in places where a large number of people gather, such as Jeongseon Casino, karaoke rooms, cruise ship cabins, and churches.

The sterilizer or sterilization lamp according to an embodiment of the present invention has a sterilization effect against avian influenza, foot-and-mouth disease, or norovirus as well as covid-19 virus. It can be used for sterilization against various viruses and bacteria that can be sterilized using a wavelength of 222 nm.

Therefore, it can be applied to various fields requiring sterilization, such as animals, plants, food, and the like, as well as sterilization of viruses or bacteria for facilities or devices used by people. In the case of an infectious disease, and the like, it can occur not only in humans but also in livestock, so it can be applied to breeding facilities, slaughter facilities, and local movement passages. For example, when avian influenza or foot-and-mouth disease occurs, the sterilization device according to an embodiment of the present invention can be applied to remove viruses or bacteria. It can be installed on the ceiling of a facility, such as a breeding facility or a slaughterhouse, and light can be irradiated in the direction of the movement passage from the ceiling, left and right, and from a lower portion toward the movement passage of a livestock or the movement passage of a vehicle.

In addition, during fruit shipment and storage, freshness can be maintained by removing fungi such as strawberries and apples that can easily go bad, and by irradiating light with a sterilization device or a sterilization lamp according to an embodiment of the present invention, viruses can be removed from foods that can cause illness due to norovirus when consumed by humans, such as seafood such as oysters and sashimi. For example, sterilization can be performed with a portable sterilizer, or sterilization can be performed on food requiring sterilization by being installed in a storage device such as a refrigerator for storage. It can also be used to perform sterilization during food processing or food storage in food processing plants and the like.

In addition, it can be applied to various facilities, devices or locations capable of sterilization using a sterilization device or sterilization lamp according to an embodiment of the present invention, that is, a wavelength of 222 nm. The sterilization device or sterilization lamp according to an embodiment of the present invention may be implemented in various forms suitable for facilities, devices, or locations being applied therewith.

Figure 13:
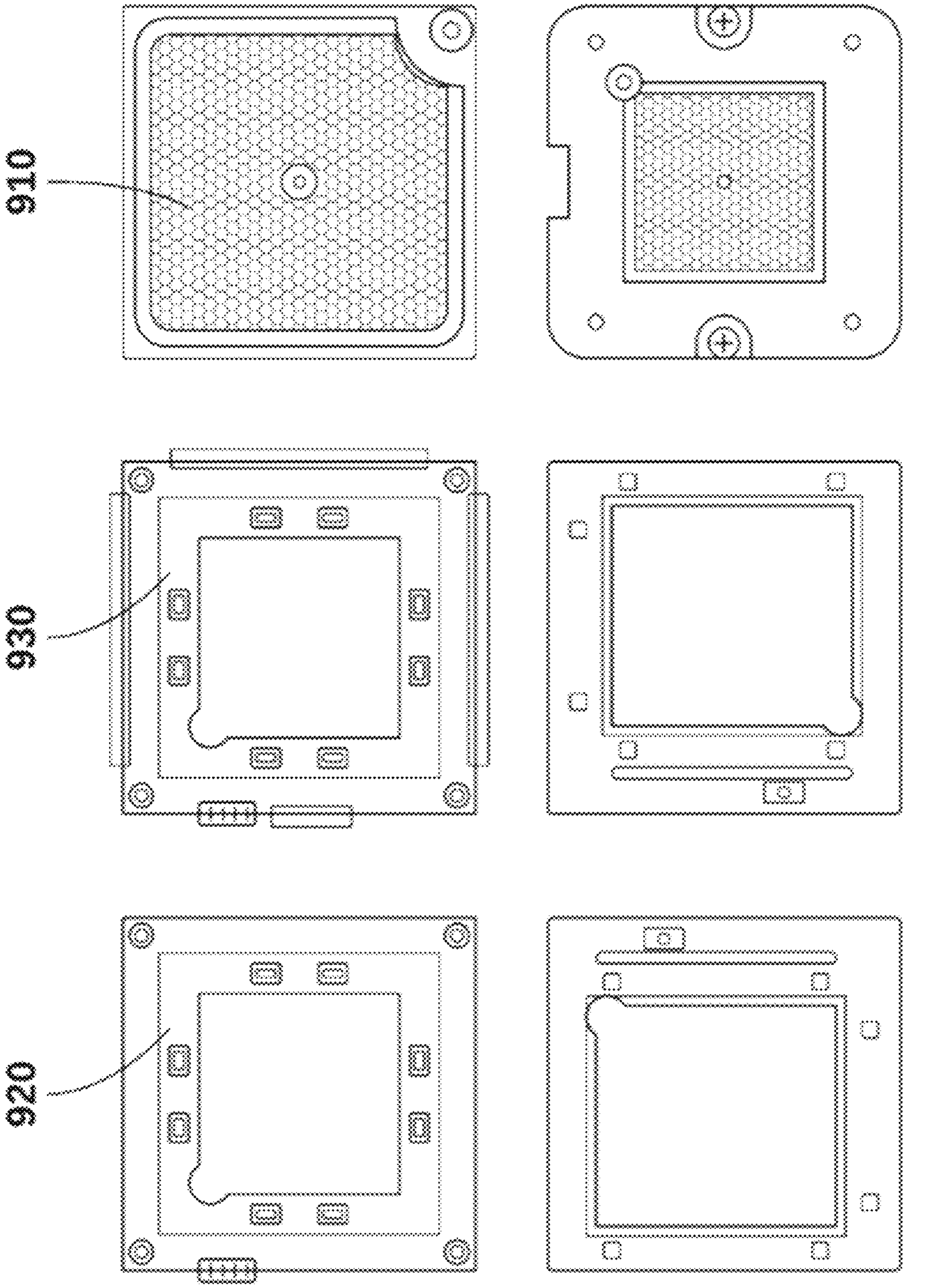

FIG. 13 shows an actual embodiment of a lamp 910, a front electrode layer 920, and a rear electrode layer 930, the lamp 910 is formed in a flat shape to emit surface light, and holes may be formed in the front electrode layer 920 and the rear electrode layer 930 so that a light can be emitted. In addition, a coupling unit may be formed at one corner so that the lamp 910, the front electrode layer 920, and the rear electrode layer 930 can be firmly coupled. A light source or conductive lines of the lamp may not be formed at a position of the coupling unit.

Figure 14:
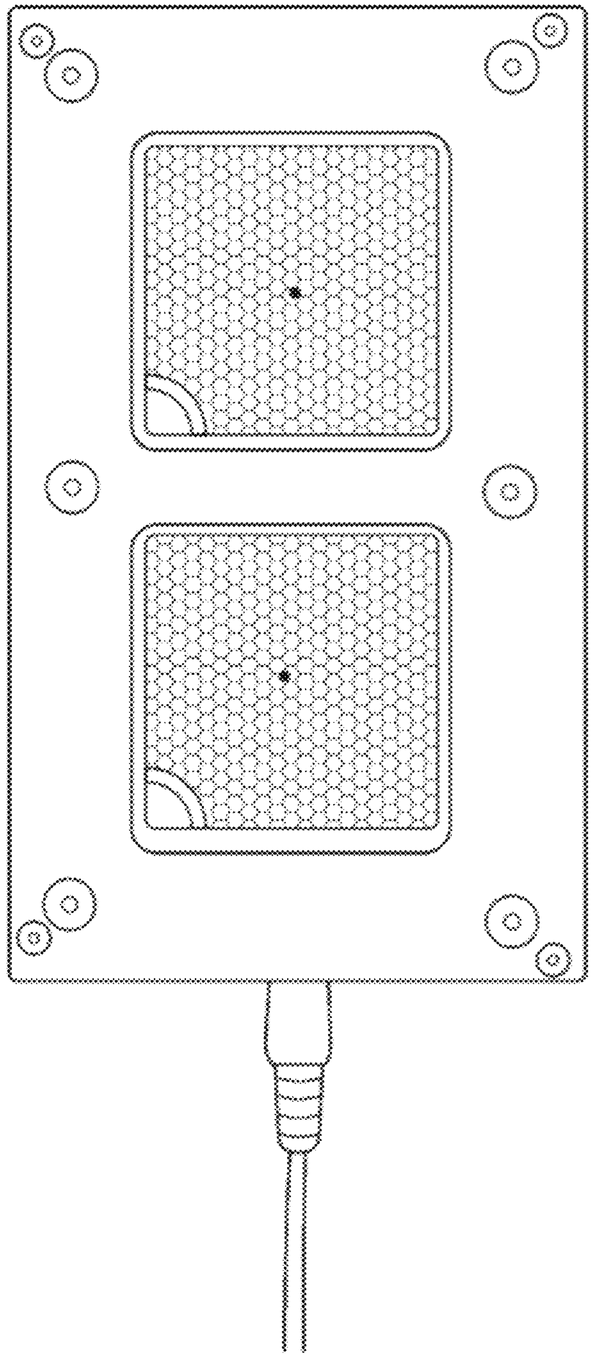
Figure 15:
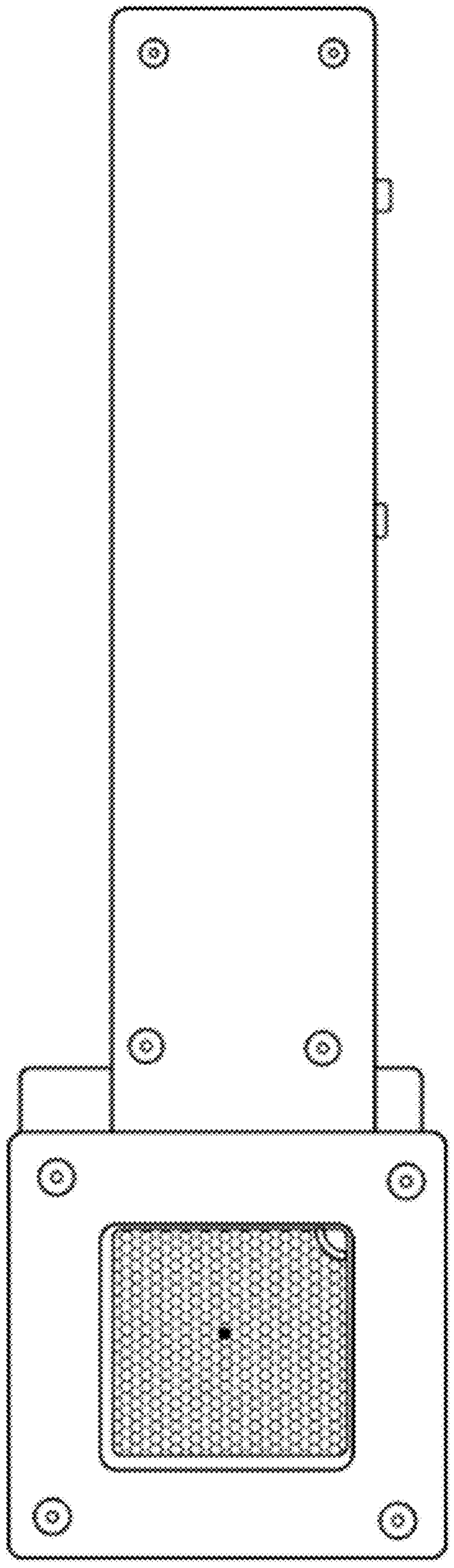
Figure 16:
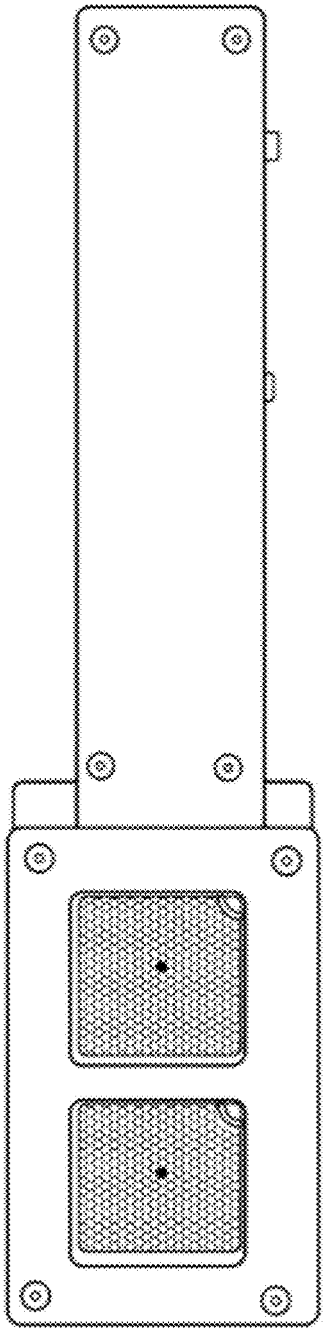

The sterilization device according to an embodiment of the present invention may be covered with a housing and provided as a single device. As shown in FIG. 14, it is implemented as a square device to which two sterilization lamps are applied, or as a portable sterilization lamp having a handle unit as shown in FIGS. 15 and 16, and it can be formed in various shapes so that one or more than two sterilization lamps are applied.

Figure 17:
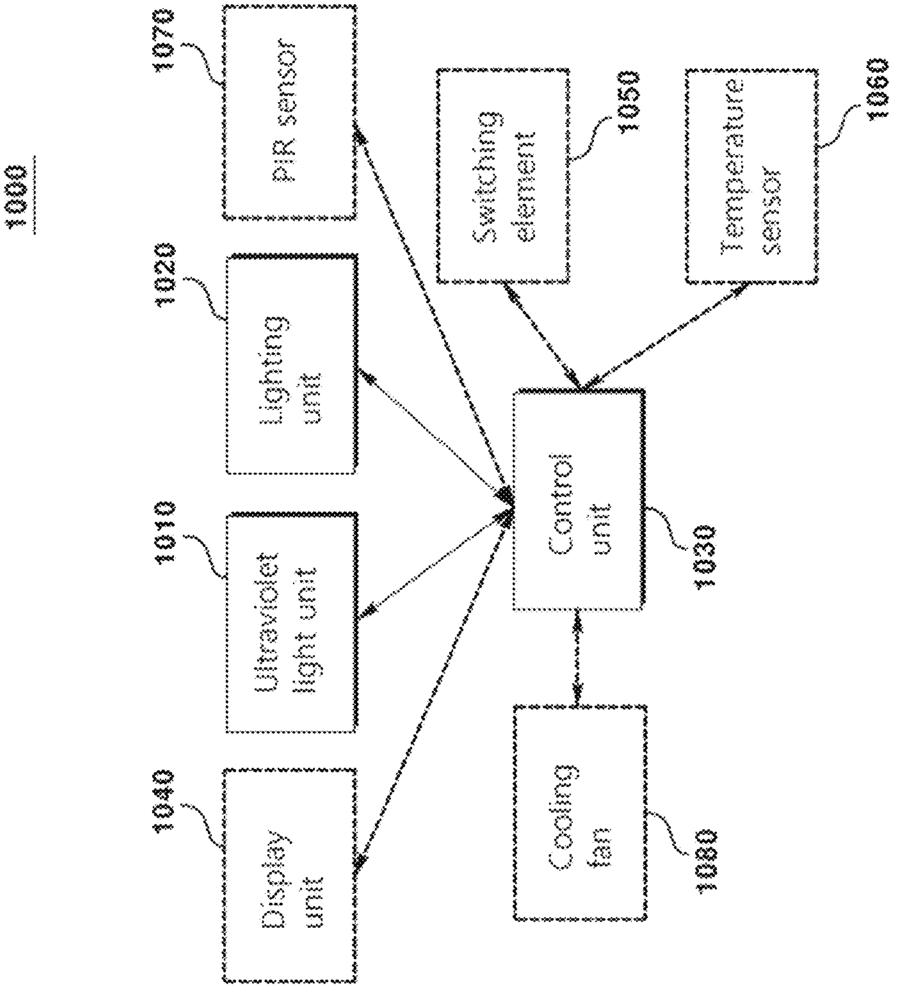
FIG. 17 is a block diagram of a sterilization lamp according to an embodiment of the present invention.

FIG. 17 is a block diagram of a sterilization lamp according to an embodiment of the present invention, and FIGS. 18 to 28 are views for explaining a sterilization lamp according to an embodiment of the present invention. The sterilization lamp according to an embodiment of the present invention is an embodiment including a lighting function for functioning as a lamp, and may include all of the configurations and functions of the sterilization device of FIGS. 1 to 16. It is natural that the sterilization devices of FIGS. 1 to 16 may include the configuration or function of the sterilization lamp including the lighting function described herein below.

The sterilization lamp 1000 according to an embodiment of the present invention may be configured with an ultraviolet light unit 1010, a lighting unit 1020, and a control unit 1030, and may include a display unit 1040, a switching element 1050, a temperature sensor 1060, a PIR sensor 1070, a cooling fan 1080, and the like.

The ultraviolet light unit 1010 includes an ultraviolet light source and a filter for filtering wavelengths of 230 to 270 nm being emitted from the ultraviolet light source. The ultraviolet light unit 1010 has a configuration corresponding to the lamp and filter described in the sterilization device of FIGS. 1 to 16, and a detailed description of the ultraviolet light unit 1010 may correspond to a detailed description of the sterilization device of FIGS. 1 to 16.

The ultraviolet light source of the ultraviolet light unit 1010 may emit ultraviolet light of wavelengths of 200 to 230 nm to kill viruses, bacteria, and the like. Here, the ultraviolet light source may be an excimer lamp (microplasma lamp) using KrCl as a light emitting gas. The ultraviolet light source of the ultraviolet light unit 1010 may be implemented in a flat shape.

The filter of the ultraviolet light unit 1010 is coated or laminated on the light-exiting surface of the ultraviolet light source to filter wavelengths of 230 to 270 nm, thereby preventing light having wavelengths harmful to the human body from being emitted to the outside. It is possible to sterilize using light having wavelengths of 200 to 230 nm that has passed through the filter. In particular, it is possible to sterilize by removing viruses, bacteria, spores, and the like using a light having a wavelength of 222 nm.

The filter of the ultraviolet light unit 1010 may convert, absorb or reflect a light having wavelengths of 230 to 270 nm into a light having a different wavelength in order to prevent a light having wavelengths of 230 to 270 nm from being emitted through the filter. The filter may include a nanophosphor that converts a light having wavelengths of 230 to 270 nm into a light having a different wavelength. Here, the nanophosphor may convert a light having wavelengths of 230 to 270 nm into a light having a wavelength of 550 nm. As shown in FIG. 4, the nanophosphor included in the filter may be a nano-fluorescent material that converts wavelengths (410) of 230 to 270 nm into a wavelength (420) of 550 nm. The nanophosphor may include $LaPO_4:Ce^{3+}\cdot Tb^{3+}$. Here, $LaPO_4:Ce^{3+}\cdot Tb^{3+}$ is the chemical structure of nanophosphor, and $LaPO_4:Ce^{3+}\cdot Tb^{3+}$ has a characteristic of absorbing a light having wavelengths of 230 to 270 nm and emitting a light having a wavelength of 550 nm. That is, it converts a light having wavelengths of 230 to 270 nm, which is toxic, into a light having a wavelength of 550 nm, which is harmless.

The nanophosphor may be formed into particles of a predetermined size, and may be mixed with a polymer material such as urethane, resin, or resin to form the filter 140. The nanophosphor may be formed to have particle sizes of 0.1 to 5 nm or less, and may be formed to have a particle size of 3 nm or less. Or, the nanophosphor may be laminated on an upper portion or a lower portion of a polymer layer containing a polymer material. At this time, it may be formed to have thicknesses of 0.1 to 20 nm, and may be formed in a planar shape by a laminating method such as coating. It is natural that nanophosphor particles can be formed in various sizes, ratios, or thicknesses for converting a light having thicknesses of 230 to 270 nm wavelengths into a light having other wavelengths.

A filter of the ultraviolet light unit 1010 may include a thin film coating that blocks a predetermined range of light. In addition to or together with the method of converting the wavelength of a light using nanophosphor, it is possible to block light of a specific wavelength. Here, the thin film coating may be a thin film containing aluminum (Al) and tin (Sn) that blocks the light having wavelengths of 230 to 270 nm. At this time, the thin film coating can be formed by mixing aluminum and tin to form a thin film, or formed of an aluminum thin film layer and a tin thin film layer. When aluminum and tin are mixed, the proportion of tin may be 0.01 to 40% or 0.01 to 20%. The remaining proportion may be aluminum or may further include other additives and the like. When formed of an aluminum thin film layer and a tin thin film layer, each thin film layer may be formed in a planar shape, and a tin thin film layer may be formed at an upper portion of the aluminum thin film layer or an aluminum thin film layer may be formed at an upper portion of the tin thin film layer. Or, one or more tin thin film layers and one or more aluminum thin film layers may be sequentially formed. The thickness of the thin film layer of tin may be 0.1 to 30 Å (angstroms) or 0.0001 to 20 Å. The aluminum thin film layer may have a thickness of 0.1 to 30 Å or more. Here, it is natural that the mixing ratio of aluminum and tin forming the thin film coating or the thickness of the aluminum thin film layer and the tin thin film layer may be formed in various ways to a mixing ratio or thickness that blocks lights having wavelengths of 230 to 270 nm A filter of the ultraviolet light unit 1010 may be formed as a thin film coating at an upper portion of the polymer material layer containing the nanophosphor particles. By using nanophosphor and thin film coating, a light having wavelengths of 230 to 270 nm, which is toxic, is converted, and may block a light having wavelengths of 230 to 270 nm. By converting a light having wavelengths of 230 to 270 nm, which is toxic, into a light having a different wavelength using nanophosphor, and at the same time, by blocking lights having wavelengths of 230 to 270 nm using a thin film coating, the lights having toxic wavelengths affecting the human body can be safely blocked in two ways.

The ultraviolet light unit 1010 may include a front electrode layer and a rear electrode layer. The front electrode layer is bonded to an upper portion of the planar ultraviolet light source unit including the ultraviolet light source, and the rear electrode layer is bonded to a lower portion of the ultraviolet light source unit to supply power to the ultraviolet light source unit.

The lighting unit 1020 includes an LED light source. The lighting unit 1020 may emit light of a wavelength corresponding to visible light for general illumination. The light source may include various light sources that emit light for illumination, and may include various light emitting devices such as LED light sources.

Through this, it is possible to provide a sterilization and lighting function by emitting light using an ultraviolet light source and an LED light source. At this time, in order to prevent interference with the light intensity of the lamp for sterilization of the light emitted from the LED light source, the temperature of the LED color can be applied from 2800K to 6000K. For example, 3000K, 4000K, 5400K, and the like may be applied. The brightness of the LED may be 800 to 1000 Lm so as not to interfere with an ultraviolet light source including 222 nm. For example, an LED with a brightness of 8 W can be used for 800 to 1000 Lm. When forming LEDs with LED color temperatures of 3000K, 4000K, and 5400K at 900 lm and 1000 lm LED brightness together with a 222 nm microplasma lamp, it can be confirmed that the intensity of the 222 nm microplasma lamp is not affected, and it can be confirmed that the sterilization function does not deteriorate even if the LED for lighting is formed together.

| LED Brightness | LED color Temperature | Ratio to the intensity (3.6E+0.3) of 222 nm microplasma lamp |
|---|---|---|
| 900 Lm | 3000 K. | 100% |
| | 4000 K. | 100% |
| | 5000 K. | 100% |
| 1000 Lm | 3000 K. | 100% |
| | 4000 K. | 100% |
| | 5000 K. | 100% |

The LED light source may be arranged at an edge of the ultraviolet light unit 1010, that is, at the edge of the ultraviolet light unit 1010, and the 222 nm plasma lamp may be arranged at the center of each lamp or at an appropriate distance from the LED light source. An ultraviolet light unit 1010 including a 222 nm plasma lamp may be formed at the center, and a lighting unit 1020 including an LED light source may be disposed at an edge. Or, the lighting unit 1020 may be disposed at the center, the ultraviolet light unit 1010 may be disposed at an edge, and the lighting unit 1020 may be disposed at various positions.

In addition to the LED light source, various light sources such as an incandescent light bulb may be included. At this time, it can be formed to have light characteristics that do not interfere with an ultraviolet light source including 222 nm. The control unit 1030 controls on and off of the ultraviolet light unit 1010 and the lighting unit 1020 and supplies power. The control unit 1030 may be formed on a substrate to control the operation of the ultraviolet light unit 1010 and the lighting unit 1020 or other components and to supply power. The control unit 1030 may include a control element such as MICOM.

The control unit 1030 may control on and off of the ultraviolet light unit 1010 and the lighting unit 1020 and supply power according to a user's command. When a user turns on or off a switch, on and off of the ultraviolet light unit 1010 and the lighting unit 1020 may be controlled to correspond to the corresponding command.

In addition, it includes a motion detection sensor such as a PIR sensor 1070 that detects motion in a predetermined region so that it can automatically operate without a user's control operation, and the control unit 1030 may turn on the ultraviolet light unit 1010 according to motion detection of the PIR sensor 1070. Through this, when a person passes through the region, sterilization can be performed.

A light for sterilization being emitted from the ultraviolet light unit 1010 removes wavelengths harmful to the human body, but it may be desirable not to directly irradiate the human body for a long time. In order to limit the irradiation time, the control unit 1030 controls the ultraviolet light unit to operate for a first time period, and turns off the ultraviolet light unit for a second time period in the middle of operating for the first time period. The ultraviolet light unit may be controlled to include one or more rest periods. Here, the first time period may be determined by law or regulation, or may be set by a test result determined to be harmless within a range to the human body or by a user. The first time period may be a time period within a certain period. For example, the first time period may be 8 hours, and may be 8 hours within 24 hours.

Figure 18:
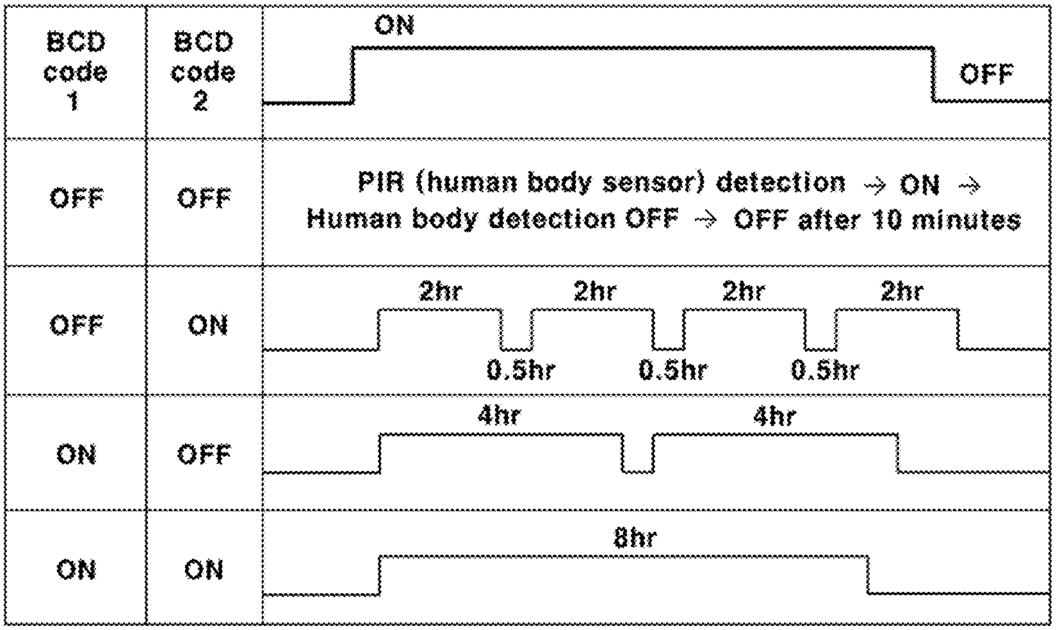
FIGS. 18 to 28 are views for explaining a sterilization lamp according to an embodiment of the present invention.

The control unit 1030 may continuously operate the ultraviolet light unit 1010 for a first time period or may apply a rest period for turning off the ultraviolet light unit 1010 for a second time period. Here, the second time period, which is a rest period, may not be included in the first time period. For example, when the first time period is 8 hours and the second time period is 30 minutes, the time to maintain the on state may be controlled to be 8 hours except for the rest period of 30 minutes. Or, it is natural that the second time period may be included in the first time period. The rest period can be one or more than two. At this time, binary coded decimal (BCD) code allows to set whether to apply a rest period or whether to control continuously. A two-digit BCD code setting is available. For example, as shown in FIG. 18, when both BCDs 1 and 2 are OFF, the human body detection sensor can be turned on and off under specific conditions, such as when a human body is detected. If BCD 1 and 2 are OFF and ON, 8 hours can be turned on by repeating the rest period three times, that is, 2 hours on and 30 minutes off. If BCD 1 and 2 are ON and OFF, it can be turned on for 8 hours by one rest period, that is, 4 hours on, 30 minutes off, and 4 hours on. If both BCD 1 and 2 are ON, it can be continuously turned on for 8 hours without a rest period. In addition, it is natural that the first time period, the second time period, the number of rest periods, and the like can be set variously.

The control unit 1030 may turn off the ultraviolet light unit 1010 and display replacement information for the ultraviolet light unit 1010 when the cumulative operating time of the ultraviolet light unit 1010 is greater than or equal to a threshold value. The lifetime of the ultraviolet light unit 1010 may be limited, and a counter for counting the accumulated operation time of the ultraviolet light unit 1010 may be included to check the lifetime of the ultraviolet light unit 1010. The ultraviolet light unit 1010 may have a shorter lifespan than the lighting unit 1020; when the lifetime of the ultraviolet light unit 1010 is over, the accumulated operating time of the ultraviolet light unit 1010 is stored so that only the ultraviolet light unit 1010 can be replaced instead of the entire sterilization lamp; and when the cumulative operation time of the ultraviolet light unit 1010 is equal to or greater than the threshold value, the ultraviolet light unit 1010 may be turned off for safe operation, and replacement information on the ultraviolet light unit 1010 may be displayed. Or, replacement information for the ultraviolet light unit 1010 may be displayed without turning off the ultraviolet light unit 1010. Here, the threshold may be set using a design specification of the ultraviolet light unit 1010 or a lifetime derived through testing. For example, 3000 hours can be set as the threshold. When the cumulative operation time of the ultraviolet light unit 1010 exceeds 3000 hours, replacement information indicating that replacement is required may be provided to the user.

In order to provide operation information of the ultraviolet light unit 1010 to a user, a display unit 1040 displaying operation information of the ultraviolet light unit 1010 may be included. The display unit 1040 may display whether the ultraviolet light unit 1010 is operating, whether it is replaced, or whether it is out of order. When the ultraviolet light unit 1010 operates, it is displayed in a first color; when the cumulative operating time of the ultraviolet light unit 1010 is greater than or equal to the threshold value, a second color is displayed; and when the ultraviolet light unit 1010 does not operate normally, the second color may flicker (blink). Here, the first color may be green, and the second color may be red, but is not limited thereto.

Components of the sterilization lamp, such as the ultraviolet light unit 1010, may include a temperature sensor 1060 in order to operate normally. The switching element 1050 that turns on and off the ultraviolet light unit 1010 may generate the most heat among internal components, and when a lot of heat is generated, a breakdown of the ultraviolet light unit 1010 may occur. In order to prevent failure of the switching element 1050 due to heat generation, the control unit 1030 may turn off the ultraviolet light unit 1010 when the temperature measured by the temperature sensor 1060 is greater than or equal to a threshold value. The temperature sensor 1060 may directly measure the temperature of the switching element 1050, or measure the temperature of a substrate on which the switching element 1050 is mounted, or the inside of a sterilization lamp. For example, if the temperature of the switching element 1050 is 100 degrees or more, the ultraviolet light unit 1010 is turned off, and when it is determined that the ultraviolet light unit 1010 does not operate normally, the second color may flicker (blink). In addition, the control unit 1030 may lower the temperature in the sterilization lamp by operating the cooling fan 1080 according to the temperature measured by the temperature sensor 1060. Or, the cooling fan 1080 may be operated when the ultraviolet light unit 1010 is operating.

Figure 19:
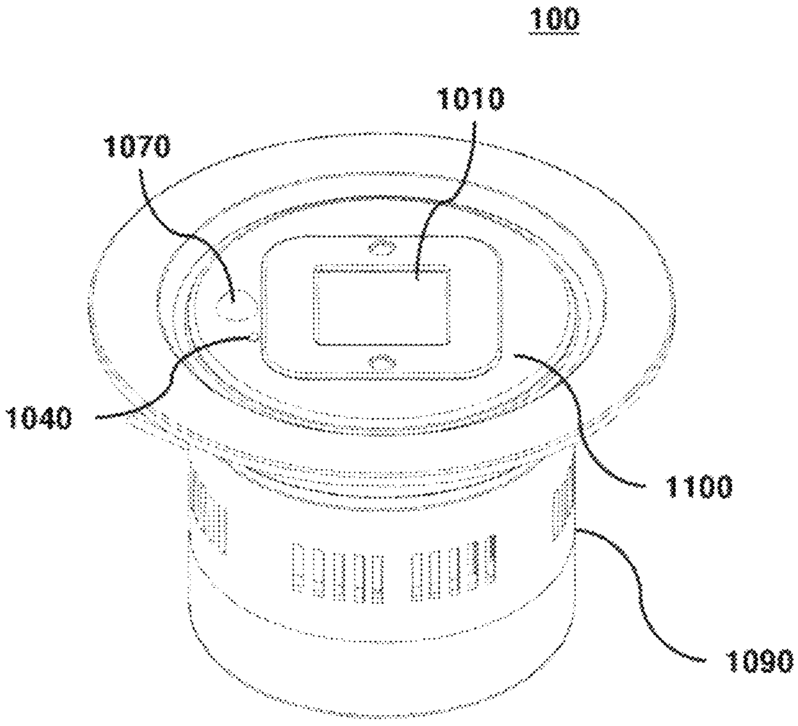
Figure 20:
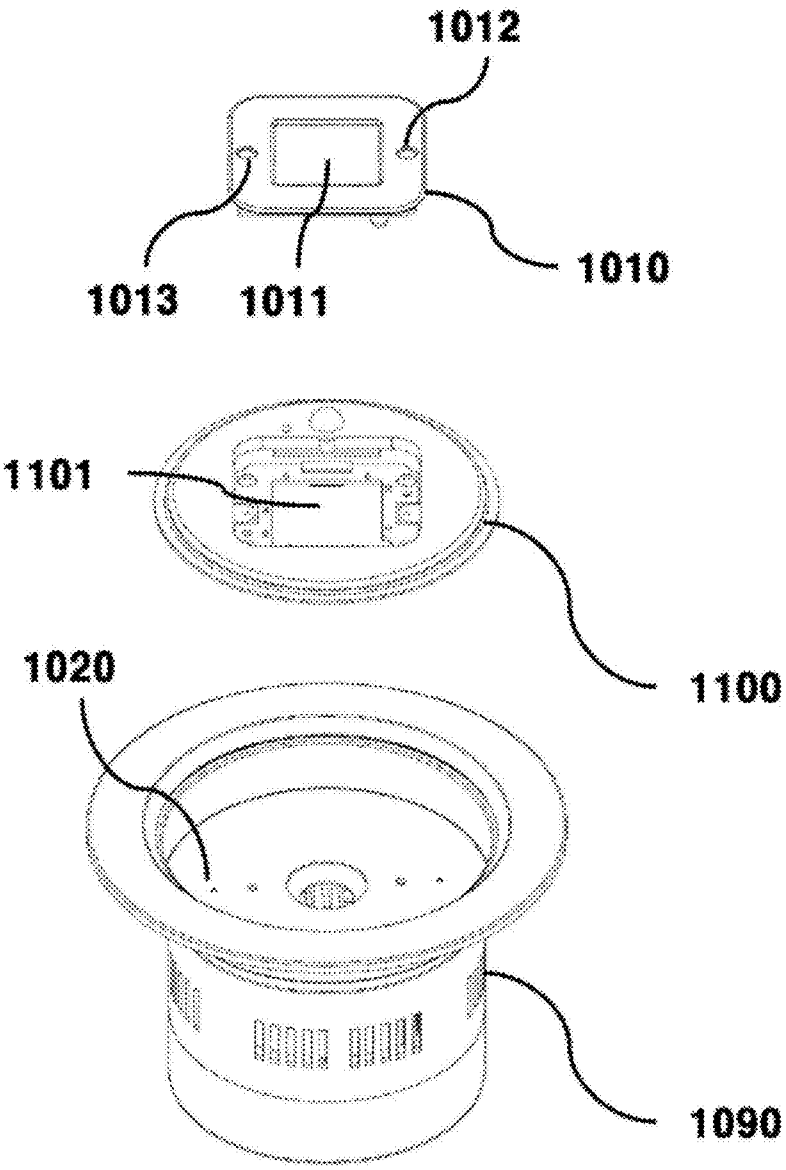
Figure 21:
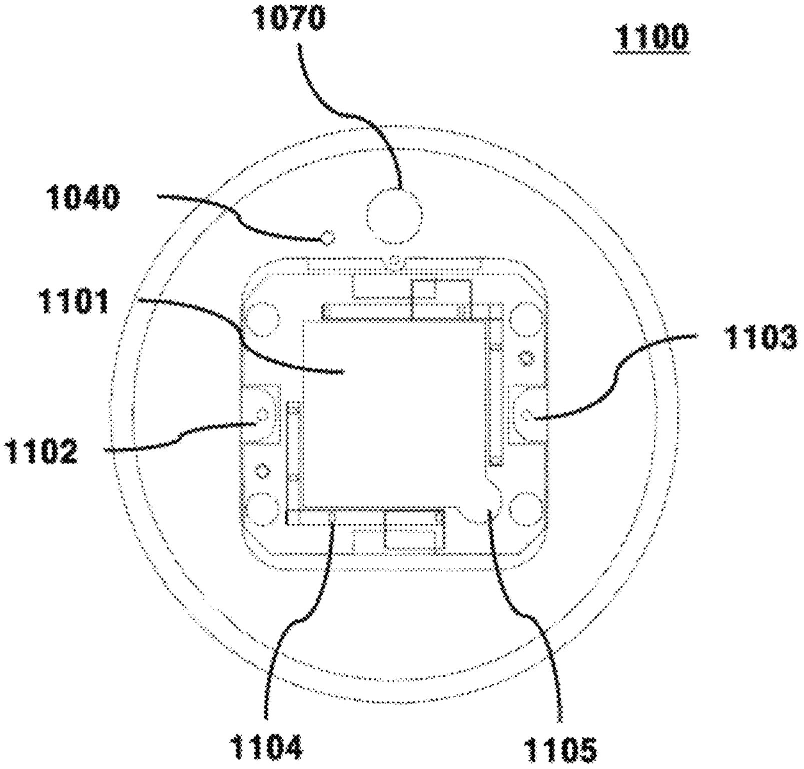
Figure 22:
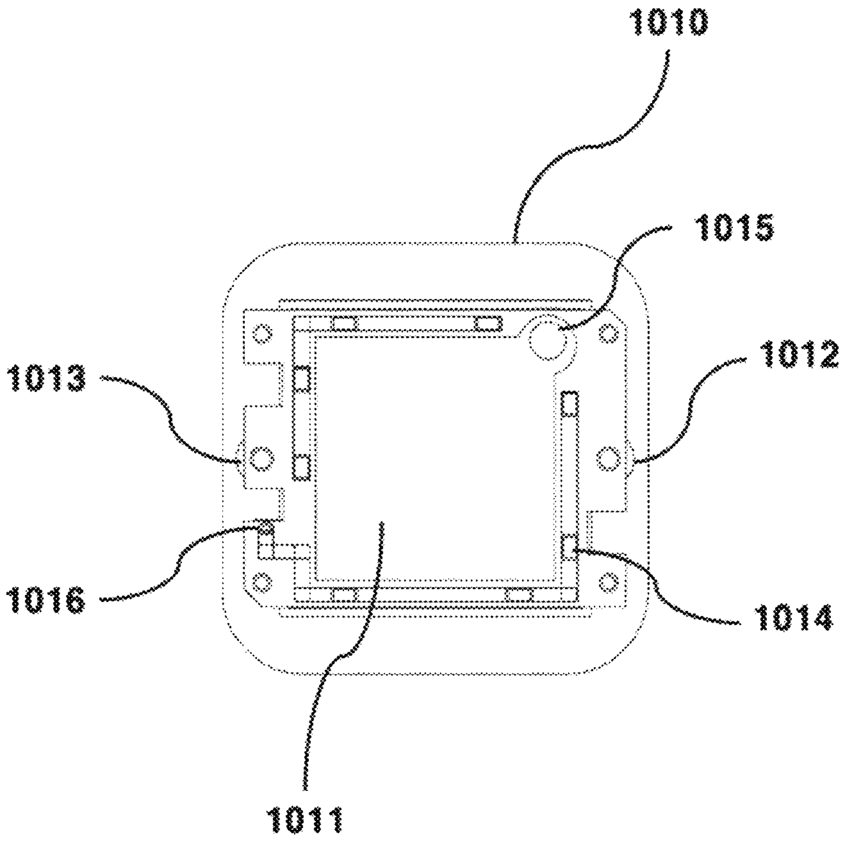

A sterilization lamp according to an embodiment of the present invention may be implemented as shown in FIGS. 19 to 20. An ultraviolet light unit 1010, a lighting unit 1020, and a control unit 1030 are disposed inside the housing 1090 and are located at an upper portion of the housing in a direction of a light-exiting surface from which light is emitted; and an ultraviolet light unit accommodating unit 1101 accommodating the ultraviolet light unit 1010 may include a cover glass 1100 being formed at the center. The ultraviolet light unit 1010 may be disposed in an ultraviolet light unit accommodating unit 1101 on the cover glass 1100, and a display unit 1040, a PIR sensor 1070, and the like may be disposed.

The ultraviolet light unit 1010 may include an ultraviolet light source unit 1011 in which an ultraviolet light source is disposed, and may include coupling units 1012 and 1013 capable of detachably attaching it for replacement.

The cover glass 1100 includes an ultraviolet light unit accommodating unit 1101 accommodating an ultraviolet light unit 1010 in the center, and an outer region of the ultraviolet light unit accommodating unit 1101 may be transparent or translucent so that a light for illumination of the lighting unit 1020 is emitted.

The ultraviolet light unit accommodating unit 1101 may include coupling units 1102 and 1103 in which the ultraviolet light unit 1010 is attachable and detachable in order to replace the ultraviolet light unit 1010 whose lifetime is over. The coupling units 1102 and 1103 of the ultraviolet light unit accommodating unit 1101 and the coupling units 1012 and 1013 of the ultraviolet light unit are respectively formed with coupling holes and may be screw-coupled together through screws. Or, it is natural that it can be coupled in various forms such as fit-coupling and hook-coupling.

The lighting unit 1020 where the LED light source is disposed emits light through the cover glass 1100, and may be disposed at a lower portion of the circumferential region of the ultraviolet light unit accommodating unit 1101 of the cover glass 1100 in order to prevent light from being blocked by the ultraviolet light unit accommodating unit 1101 of the cover glass 1100.

Inside the housing 1090, a board on which a control unit 1030, a microcontroller, is mounted may be disposed; a switching element 1050 and the like are mounted on the board; and terminals for transmitting and receiving signals to and from or supply power to internal components such as a power supply being connected to an external power source or battery, a display unit 1040 that is connected, an ultraviolet light unit 1010, a lighting unit 1020, a PIR sensor 1070, a cooling fan 1080, a temperature sensor 1060, and the like may be mounted.

The ultraviolet light unit 1010 is accommodated in the ultraviolet light unit accommodating unit 1101 and is controlled on and off by the control unit 1030 and supplied with power through the ultraviolet light unit accommodating unit 1101. To this end, an electrode 1104 being in contact with the ultraviolet light unit 1010 may be formed in the ultraviolet light unit accommodating unit 1101, and conductive lines may be formed along the electrode. The ultraviolet light unit 1010 is also formed with an electrode 1014 to correspond to the electrode 1104 of the ultraviolet light unit accommodating unit 1101, and may be formed with conductive lines along the electrode. The ultraviolet light unit 1010 may include a rear electrode layer and a front electrode layer, and some of the conductive lines may be connected to a terminal 1016 being connected to the front electrode layer to supply power to the front electrode layer.

In addition, in order to guide the coupling of the ultraviolet light unit 1010 and the ultraviolet light unit accommodating unit 1101, may be formed with a guide unit 1015 in the ultraviolet light unit 1010 and a guide hole 1105 in the ultraviolet light unit accommodating unit 1101. Through this, contact between the electrodes can be made accurately.

Figure 23:
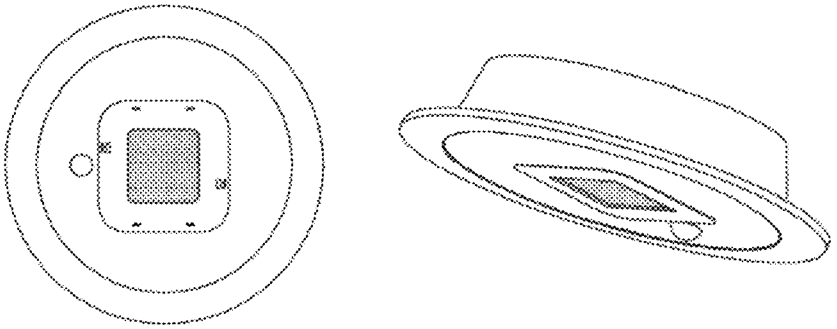
Figure 24:
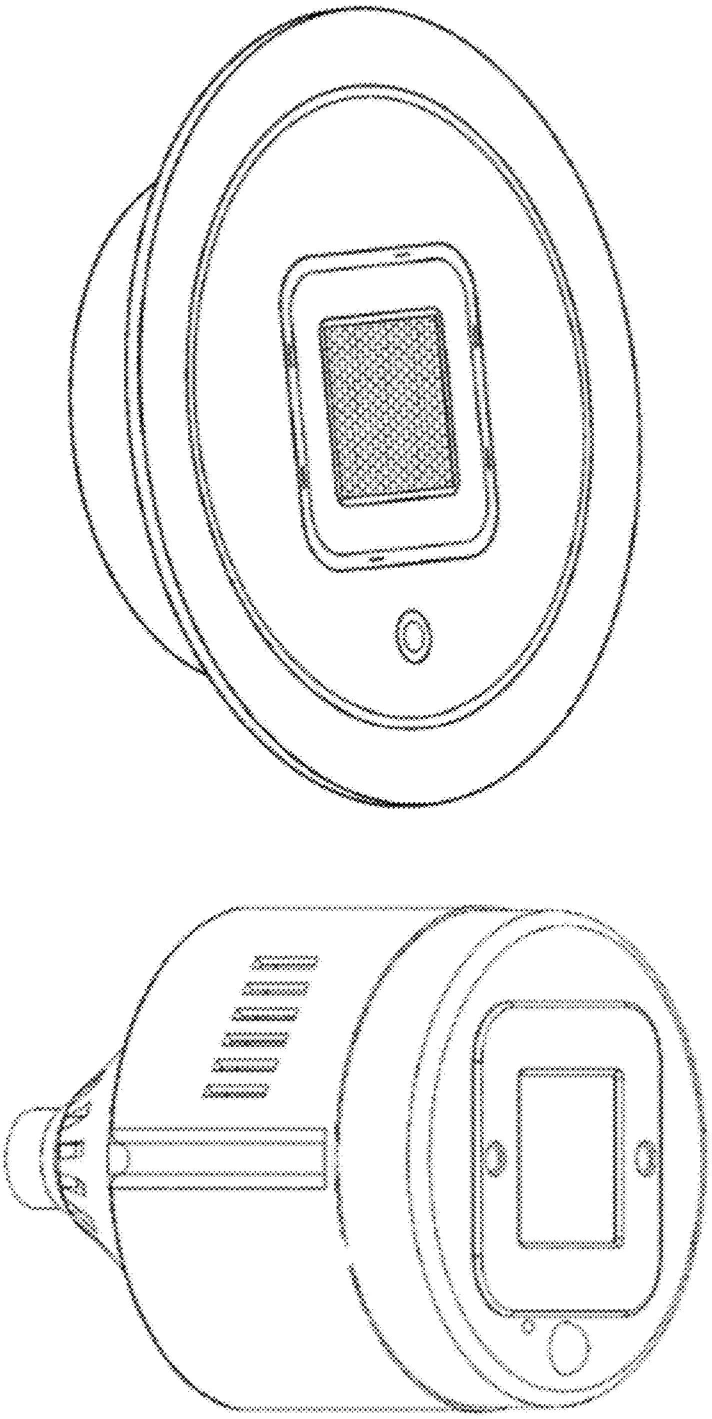
Figure 25:
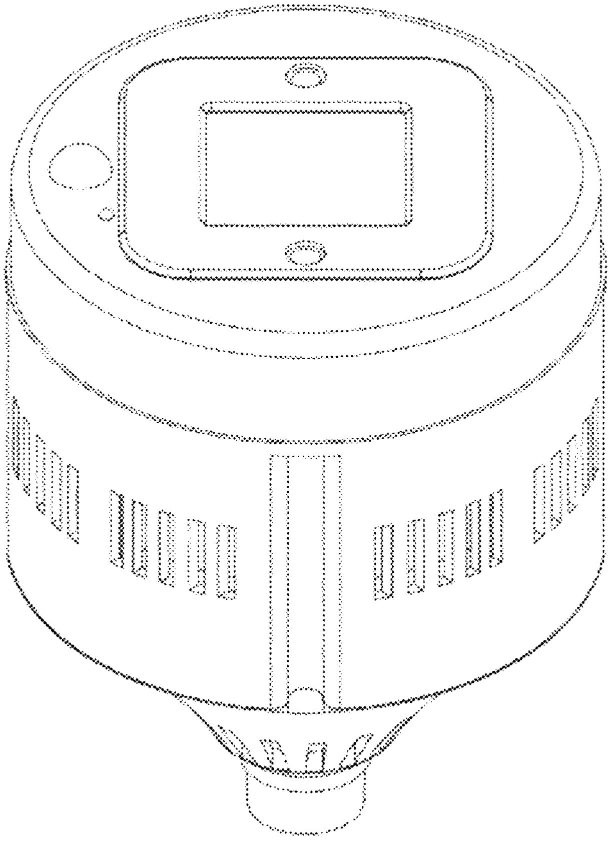
Figure 26:
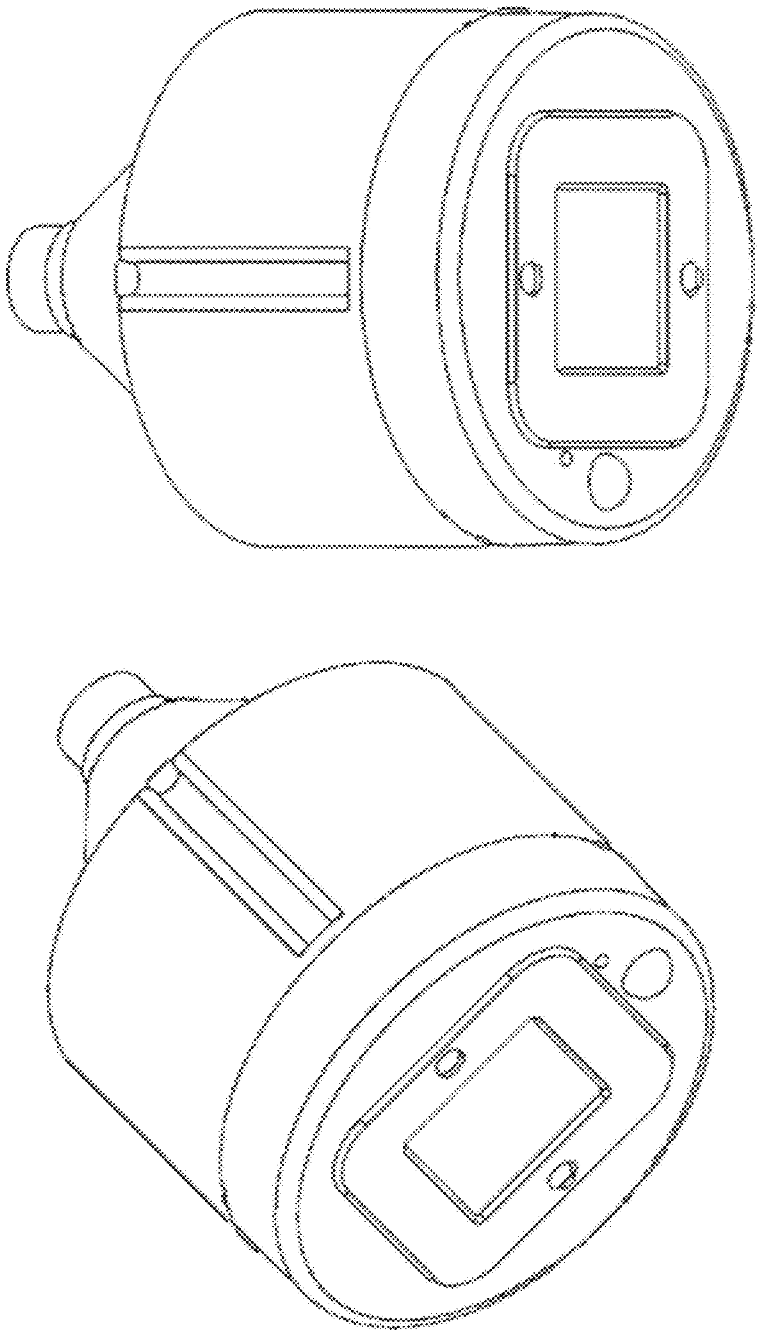
Figure 27:
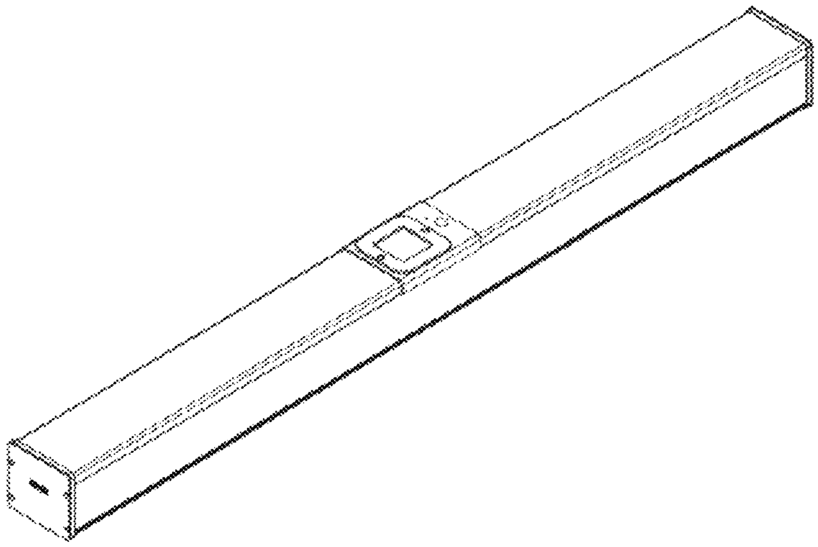
Figure 28:
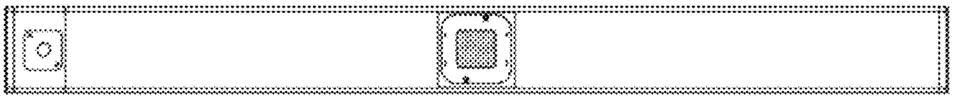

The sterilization lamp according to an embodiment of the present invention may be implemented in various lamp shapes and formed in a down light shape as shown in FIGS. 23 and 24, or formed in a bulb shape as shown in FIGS. 25 and 26, or formed in a raceway as shown in FIGS. 27 and 28, and the like, and perform sterilization. Detailed description of the sterilization lamp according to each embodiment differs only in the shape, but corresponds to the detailed description of the sterilization lamp of FIGS. 17 to 22, so overlapping description will be omitted.

The sterilization device according to an embodiment of the present invention has a 222 nm KrCl excimer lamp applied with a filter for filtering wavelengths of 230 to 270 nm, and the results of verifying the removal performance of the corona (COVID-19) virus are as follows. The distance of 4 cm of light irradiation distance and the irradiation time of 10 seconds, 20 seconds, 30 seconds, 1 minute, 2 minutes, 5 minutes, and 10 minutes were applied, and virus diluted to stock solutions, 10-1, 10-2, 10-3, 10-4, 10-5, and 10-6 in 5 wells in a 96-well plate, respectively, was inoculated using DMEM together with the control group. Vero cells were observed for 5 days after inoculation of 60 to 70% 96 well plates, and the effect of reducing the virus concentration was examined compared to the control group. The degree of virus inhibition was determined by repeating the experiment three times using the Kaerber and Reed method to calculate the virus titer; after observing cell degeneration, the virus culture medium is collected to isolate viral nucleic acids; and real-time PCR was performed using a precise Covid-19 virus diagnosis kit.

As a result of the first test, the virus removal rate is as follows.

| UV response time | $Log_{10}TCID_{50}$/ml | virus removal rate | Real-time PCR result(Ct value) |
|---|---|---|---|
| No response | 3.83 | — | 12.28 |
| 10 seconds | 2.92 | >89.0 | 15.34 |
| 20 seconds | 1.83 | >99.0 | 18.88 |
| 30 seconds | 0.67 | >99.9 | 21.48 |
| 1 minute | <0.5 | >99.9 | 0 |
| 2 minutes | <0.5 | >99.9 | 0 |
| 5 minutes | <0.5 | >99.9 | 0 |
| 10 minutes | <0.5 | >99.9 | 0 |

As a result of the second test, the virus removal rate is as follows.

| UV response time | $Log_{10}TCID_{50}$/ml | virus removal rate | Real-time PCR result(Ct value) |
|---|---|---|---|
| No response | 4.50 | — | 11.13 |
| 10 seconds | 3.60 | >90.0 | 14.72 |
| 20 seconds | 2.23 | >99.6 | 19.34 |
| 30 seconds | 1.48 | >99.9 | 22.37 |
| 1 minute | <0.5 | >99.99 | 32.13 |
| 2 minutes | <0.5 | >99.99 | 0 |
| 5 minutes | <0.5 | >99.99 | 0 |
| 10 minutes | <0.5 | >99.99 | 0 |

As a result of the third test, the virus removal rate is as follows.

| UV response time | $Log_{10}TCID_{50}$/ml | virus removal rate | Real-time PCR result(Ct value) |
|---|---|---|---|
| No response | 4.33 | — | 11.08 |
| 10 seconds | 3.33 | >90.0 | 15.67 |
| 20 seconds | 1.83 | >99.3 | 18.57 |
| 30 seconds | 1.17 | >99.9 | 23.65 |
| 1 minute | <0.5 | >99.99 | 31.37 |
| 2 minutes | <0.5 | >99.99 | 0 |
| 5 minutes | <0.5 | >99.99 | 0 |
| 10 minutes | <0.5 | >99.99 | 0 |

As the above results, it was confirmed that more than 99.99% of the corona virus was removed when irradiated for 1 minute or more, 99.9% when irradiated for 30 seconds, and 90% or more when irradiated for 10 seconds.

In this way, the sterilization device according to an embodiment of the present invention has high sterilization ability and is harmless to the human body by removing wavelengths harmful to the human body. In addition, when formed in the form of a lighting device, it can be applied together with LED lighting anywhere in the space with a ceiling, and when implemented in a portable form, sterilization becomes possible in more diverse locations.

Those skilled in the art related to the present embodiment will be able to understand that it may be implemented in a modified form within a range that does not deviate from the essential characteristics of the above description. Therefore, the disclosed methods should be considered from an explanatory point of view, not from a limited point of view. The scope of the present invention is shown in the claims rather than the foregoing description, and all differences within the equivalent scope will be construed as being included in the present invention.

The invention claimed is:

1. A sterilization lamp comprising:

an ultraviolet light unit including an ultraviolet light source and a filter for filtering wavelengths of 230 to 270 nm, emitted from the ultraviolet light source;

a lighting unit including an LED light source; and a control unit which controls on and off of the ultraviolet light unit and the lighting unit and supplies power, wherein the filter includes a nanophosphor which is 3 nm or less, and the nanophosphor converts the light having wavelengths of 230 to 270 nm into light of another wavelength, and wherein the nanophosphor includes $LaPO_4:Ce^{3+}\cdot Th^{3+}$.

2. The sterilization lamp according to claim 1, wherein the control unit controls the ultraviolet light unit to operate for a first time period, and wherein in the middle of the operation during the first time, the control unit controls the ultraviolet light to include one or more rest periods in which the ultraviolet light unit is turned off for a second time period.

3. The sterilization lamp according to claim 1, wherein the control unit turns off the ultraviolet light unit and display replacement information for the ultraviolet light unit when the cumulative operating time of the ultraviolet light unit is greater than or equal to a threshold value.

4. The sterilization lamp according to claim 1, including:

a display unit for displaying operation information of the ultraviolet light unit wherein it is displayed in a first color when the ultraviolet light unit is operating, wherein a second color is displayed when the cumulative operating time of the ultraviolet light unit is greater than or equal to a threshold value, and wherein the second color flickers when the ultraviolet light unit is not operating normally.

5. The sterilization lamp according to claim 1, including:

a switching element for turning on and off the ultraviolet light unit; and a temperature sensor for measuring a temperature inside the switching element, a substrate on which the switching element is mounted, or a sterilization lamp, and wherein the control unit turns off the ultraviolet light unit when the temperature measured by the temperature sensor is greater than or equal to a threshold value.

6. The sterilization lamp according to claim 1, including:

a PIR sensor which detects motion in a predetermined region, wherein the control unit turns on the ultraviolet light unit according to motion detection of the PIR sensor.

7. The sterilization lamp according to claim 1, including:

a housing in which the ultraviolet light unit, the lighting unit, and the control unit are disposed therein, wherein the housing includes a cover glass located at an upper portion of the housing and being formed with an ultraviolet light unit accommodating unit for accommodating the ultraviolet light unit at the center thereof, and wherein the ultraviolet light unit accommodating unit includes a coupling unit to which the ultraviolet light unit is detachably attachable.

8. The sterilization lamp according to claim 7, wherein the LED light source is disposed at a lower portion of a circumferential region of the ultraviolet light unit accommodating unit of the cover glass.

9. A sterilization lamp comprising:

a planar lamp in which at least one or more light sources emitting 222 nm ultraviolet rays are disposed at an inner region;

a filter being coated or laminated on a light-exiting surface of the lamp to filter light having a wavelengths of 230 to 270 nm; and a power supply unit supplying power to the lamp, wherein the filter includes a nanophosphor having a size of 3 nm or less to convert light having a wavelengths of 230 nm to 270 nm into a light having a different wavelength, and wherein the nanophosphor includes $LaPO_4:Ce^{3+}\cdot Tb^{3+}$.

* * * * *